US009766552B2

(12) United States Patent
Van Beurden

(10) Patent No.: US 9,766,552 B2
(45) Date of Patent: Sep. 19, 2017

(54) METHODS AND APPARATUS FOR CALCULATING ELECTROMAGNETIC SCATTERING PROPERTIES OF A STRUCTURE AND FOR RECONSTRUCTION OF APPROXIMATE STRUCTURES

(71) Applicant: ASML Netherlands B.V., Veldhoven (NL)

(72) Inventor: Martijn Constant Van Beurden, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 17 days.

(21) Appl. No.: 14/915,804

(22) PCT Filed: Aug. 8, 2014

(86) PCT No.: PCT/EP2014/067063
§ 371 (c)(1),
(2) Date: Mar. 1, 2016

(87) PCT Pub. No.: WO2015/032586
PCT Pub. Date: Mar. 12, 2015

(65) Prior Publication Data
US 2016/0223916 A1     Aug. 4, 2016

Related U.S. Application Data

(60) Provisional application No. 61/875,340, filed on Sep. 9, 2013.

(51) Int. Cl.
*G01B 11/04*     (2006.01)
*G03B 27/32*     (2006.01)
(Continued)

(52) U.S. Cl.
CPC ....... *G03F 7/70483* (2013.01); *G01N 21/956* (2013.01); *G03F 7/705* (2013.01);
(Continued)

(58) Field of Classification Search
CPC ........... G01N 21/956; G01N 21/95607; G01N 21/95615; G03F 7/70483; G03F 7/705;
(Continued)

(56) References Cited

U.S. PATENT DOCUMENTS

| 6,867,866 B1 | 3/2005 | Chang et al. |
|---|---|---|
| 7,038,850 B2 | 5/2006 | Chang et al. |

(Continued)

FOREIGN PATENT DOCUMENTS

| CN | 102692823 A | 9/2012 |
|---|---|---|
| CN | 103279016 A | 9/2013 |

(Continued)

OTHER PUBLICATIONS

Delves, M. L., et al., Computational methods for integral equations. Cambridge University Press, 1985; 14 pages.
(Continued)

*Primary Examiner* — Colin Kreutzer
(74) *Attorney, Agent, or Firm* — Sterne, Kessler, Goldstein & Fox P.L.L.C.

(57) ABSTRACT

A method of calculating electromagnetic scattering properties of a structure, the structure including materials of differing properties and the structure being periodic in at least one lateral direction and extending in a vertical direction, comprises: numerically solving a volume integral equation for electromagnetic scattering for a plurality of modes in the at least one lateral direction, by performing, for each respective mode, integration (1350) of a pseudo-spectral polynomial (Chebyshev) expansion in the vertical direction multiplied by a ID Green's function using the same sample
(Continued)

points in the orthogonal direction for all of the plurality of modes. The integration is performed by solving a regularized linear system of equations between first (1116) and second (1120) discrete transformation steps to compute (1118) values of a regularized Chebyshev expansion coefficient vector ($\gamma$). Electromagnetic scattering properties of the structure are calculated using the results of the numerical solution.

12 Claims, 16 Drawing Sheets

(51) Int. Cl.
| | |
|---|---|
| *G03B 27/74* | (2006.01) |
| *G03F 7/20* | (2006.01) |
| *H01L 21/66* | (2006.01) |
| *G01N 21/956* | (2006.01) |

(52) U.S. Cl.
CPC ...... *G03F 7/70625* (2013.01); *G03F 7/70633* (2013.01); *H01L 22/12* (2013.01); *G01B 2210/56* (2013.01)

(58) Field of Classification Search
CPC . G03F 7/70625; G03F 7/70633; G03F 9/7092
USPC .................................. 355/68, 77; 356/636
See application file for complete search history.

(56) References Cited

U.S. PATENT DOCUMENTS

| | | |
|---|---|---|
| 2009/0138246 A1 | 5/2009 | Chow |
| 2011/0098992 A1 | 4/2011 | Van Beurden et al. |
| 2011/0218789 A1 | 9/2011 | Van Beurden |
| 2012/0123748 A1 | 5/2012 | Aben et al. |
| 2013/0066597 A1 | 3/2013 | Van Beurden |

FOREIGN PATENT DOCUMENTS

| | | |
|---|---|---|
| EP | 1 628 164 A | 2/2006 |
| EP | 2 068 262 A1 | 6/2009 |
| EP | 2 302 360 A2 | 3/2011 |
| EP | 2 515 168 A2 | 10/2012 |
| JP | 2013-534044 A | 8/2013 |
| TW | 200928790 A | 7/2009 |
| TW | 201303482 A | 1/2013 |
| WO | WO 2015/032586 A1 | 3/2015 |

OTHER PUBLICATIONS

Hasegawa, T., et al., "Indefinite integration of oscillatory functions by the Chebyshev series expansion". Journal of Computational and Applied Mathematics, vol. 17, 1987; pp. 21-29.

International Search Report with Search Report directed to App. No. PCT/EP2014/067063, mailed Oct. 21, 2014; 12 pages.

Kang, S.Y., et al., "Nyström-Clenshaw-Curtis quadrature for integral equations with discontinuous kernels", Mathematics of computation, vol. 72, No. 242, Mar. 2002; pp. 729-756.

Press, W.H., et al., Numerical Recipes in Fortran 77: The Art of Scientific Computing, Cambridge University Press, 2nd edition, 1992. (submitted in 21 parts).

Quarteroni, A., et al., "Polynomial Expression", Numerical Approximation of Partial Differential Equations. Springer Series in Computational Mathematics. Springer, 1994; pp. 101-127.

International Preliminary Report on Patentability and Written Opinion of the International Searching Authority directed to related International Patent Application No. PCT/EP2014/067063, issued Mar. 15, 2016; 8 pages.

METHODS AND APPARATUS FOR CALCULATING ELECTROMAGNETIC SCATTERING PROPERTIES OF A STRUCTURE AND FOR RECONSTRUCTION OF APPROXIMATE STRUCTURES

CROSS-REFERENCE TO RELATED APPLICATIONS

This application claims the benefit of U.S. provisional application 61/875,340, which was filed on Sep. 9, 2013 and which is incorporated herein in its entirety by reference.

FIELD

The present invention relates to calculation of electromagnetic scattering properties of structures.

The invention may be applied for example in metrology of microscopic structures, for example to assess critical dimensions (CD) performance of a lithographic apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is necessary to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

More generally, it would be useful to be able to compare the scattered radiation with scattering behaviors predicted mathematically from models of structures, which can be freely set up and varied until the predicted behavior matches the observed scattering from a real sample. Unfortunately, although it is in principle known how to model the scattering by numerical procedures, the computational burden of the known techniques renders such techniques impractical, particularly if real-time reconstruction is desired, and/or where the structures involved are more complicated than a simple structure periodic in one-dimension.

CD reconstruction belongs to a group of problems known under the general name of inverse scattering, in which observed data is matched to a possible physical situation. The aim is to find a physical situation that gives rise to the observed data as closely as possible. In the case of scatterometry, the electromagnetic theory (Maxwell's equations) allows one to predict what will be the measured (scattered) data for a given physical situation. This is called the forward scattering problem. The inverse scattering problem is now to find the proper physical situation that corresponds to the actual measured data, which is typically a highly nonlinear problem. To solve this inverse scattering problem, a nonlinear solver is used that uses the solutions of many forward scattering problems. In known approaches for reconstruction, the nonlinear problem is founded on three ingredients:

Gauss-Newton minimization of the difference between measured data and data computed from the estimated scattering setup;

parameterized shapes in the scattering setup, e.g. radius and height of a contact hole;

sufficiently high accuracy in the solution of the forward problem (e.g. computed reflection coefficients) each time the parameters are updated.

For CD reconstruction of 1D- or 2D-periodic structures (e.g. gratings) a Volume Integral Method (VIM) can be used to efficiently compute the solution of the pertaining scattering problem, as has been disclosed in US patent application publication no. US2011/0218789 A1 and US patent application publication no. US2011/0098992 A1, which are incorporated herein by reference. The particular choice for a spectral expansion in the plane of periodicity, results in a fully decoupled modal description in the orthogonal aperiodic direction. This modal description, which takes the form of a sequence of 1-dimensional integral equations, each with a 1D Green's function that describes the wave propagation per mode, is discretized or sampled to arrive at a numerical scheme. For a low-order discretization scheme, the structure of the 1D integral equations leads to a numerically stable and efficient O(N) algorithm for the matrix-vector product, where N is the number of samples per 1D integral equation.

The Chebyshev expansion has been known for a long time and especially its relation to the discrete cosine transformation (DCT) has been exploited to produce efficient numerical schemes for a range of numerical methods including differential equations and 1D integral equations, for example [2,4,5].

A distinct disadvantage of a low-order expansion to discretize the 1D integral equations is that the numerical discretization error converges as $O(h^2)$, where h is the mesh size. For structures that are high with respect to the wavelength along the aperiodic direction, many samples are needed to reach an acceptable level of accuracy, which in turn leads to long computation times and large memory requirements.

An approach to increase the convergence rate is then to introduce higher-order expansions with high-order polynomials, which gives rise to pseudo-spectral methods, which include Chebyshev polynomial expansions and Legendre polynomial expansions. Pseudo-spectral methods are known for their exponential convergence. However, there are two caveats with this approach: Does the high-order expansion give rise to an efficient matrix-vector product?; and is the resulting numerical scheme stable?

Chebyshev expansions yield an efficient matrix-vector product of O(N log N), owing to the use of a discrete cosine transformation (DCT). However, the stability turns out to be a substantial problem, especially for evanescent modes, e.g. the scheme presented in [2] has been found to be highly unstable for the above mentioned integral equation, as illustrated by FIG. 16 herein. Without further measures for stability, the resulting linear system of integral equations has a very high condition number and therefore it cannot be reliably solved iteratively.

SUMMARY

It is desirable in the field of semiconductor processing to rapidly perform accurate calculations of electromagnetic scattering properties.

According to a first aspect of the present invention, there is provided a method of calculating electromagnetic scattering properties of a structure, the structure including materials of differing properties and the structure being periodic in at least one lateral direction and extending in a direction orthogonal with respect to the at least one lateral direction, the method comprising:

numerically solving a volume integral equation for electromagnetic scattering for a plurality of modes in the at least one lateral direction, by performing, for each respective mode, integration of a pseudo-spectral polynomial expansion in the orthogonal direction multiplied by a 1D Green's function using the same sample points in the orthogonal direction for all of the plurality of modes, wherein the integration is performed by solving a regularized linear system of equations; and calculating electromagnetic scattering properties of the structure using results of the numerical solution.

The method may further comprise the steps of:

regularizing the linear system of equations by modifying the linear system to compensate for expansion coefficients prone to conditioning-related errors by defining an extended regularized expansion coefficient vector $(\gamma^1, \gamma^2)$;

solving the regularized linear system of equations between first and second discrete transformation steps to compute values of the regularized expansion coefficient vector $(\gamma^1, \gamma_2)$;

applying the second discrete transformation step to a non-extended part $(\gamma^{1*}, \gamma^{2*})$ of the regularized expansion coefficients vector $(\gamma^1, \gamma^2)$ to compute a regularized integral $(H_1(k), H_2(k))$ at sample points in the orthogonal direction; and wherein the step of calculating electromagnetic scattering properties of the structure uses the computed regularized integral $(H_1(k)$ and $H_2(k))$.

The step of regularizing the linear system of equations may comprise generating a function (F(k)) at sample points in the orthogonal direction, the function comprising expansion coefficients prone to conditioning-related errors, such that the modifying of the linear system compensates for the function (F(k)), and the method may further comprise the step, after the discrete transformation step, of combining the regularized integral $(H_1(k)$ and $H_2(k))$ with an extension part $(\gamma^1_{M+1}, \gamma^2_{M+1})$ of the regularized expansion coefficients vector $(\gamma^1, \gamma^2)$ multiplied by the function (F(k)) to compute a further integral $(G_1(k)$ and $G_2(k))$ at sample points in the orthogonal direction, and the step of calculating electromagnetic scattering properties of the structure may use the computed further integral $(G_1(k)$ and $G_2(k))$.

According to a second aspect of the present invention, there is provided a method of reconstructing an approximate structure of an object from a detected electromagnetic scattering property arising from illumination of the object by radiation, the method comprising the steps:

estimating at least one structural parameter;

determining at least one model electromagnetic scattering property from the at least one structural parameter;

comparing the detected electromagnetic scattering property to the at least one model electromagnetic scattering property; and determining an approximate object structure based on the result of the comparison, wherein the model electromagnetic scattering property is determined using a method according to the first aspect.

According to a third aspect of the present invention, there is provided an inspection apparatus for reconstructing an approximate structure of an object, the inspection apparatus comprising:

an illumination system configured to illuminate the object with radiation;

a detection system configured to detect an electromagnetic scattering property arising from the illumination; and a processor configured to:

estimate at least one structural parameter;

determine at least one model electromagnetic scattering property from the at least one structural parameter;

compare the detected electromagnetic scattering property to the at least one model electromagnetic scattering property; and determine an approximate object structure from a difference between the detected electromagnetic scattering property and the at least one model electromagnetic scattering property, wherein the processor is configured to determine the model electromagnetic scattering property using a method according to the first aspect.

According to a fourth aspect of the present invention, there is provided a computer program product containing one or more sequences of machine-readable instructions for calculating electromagnetic scattering properties of a structure, the instructions being adapted to cause one or more processors to perform a method according to the first aspect.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 1:
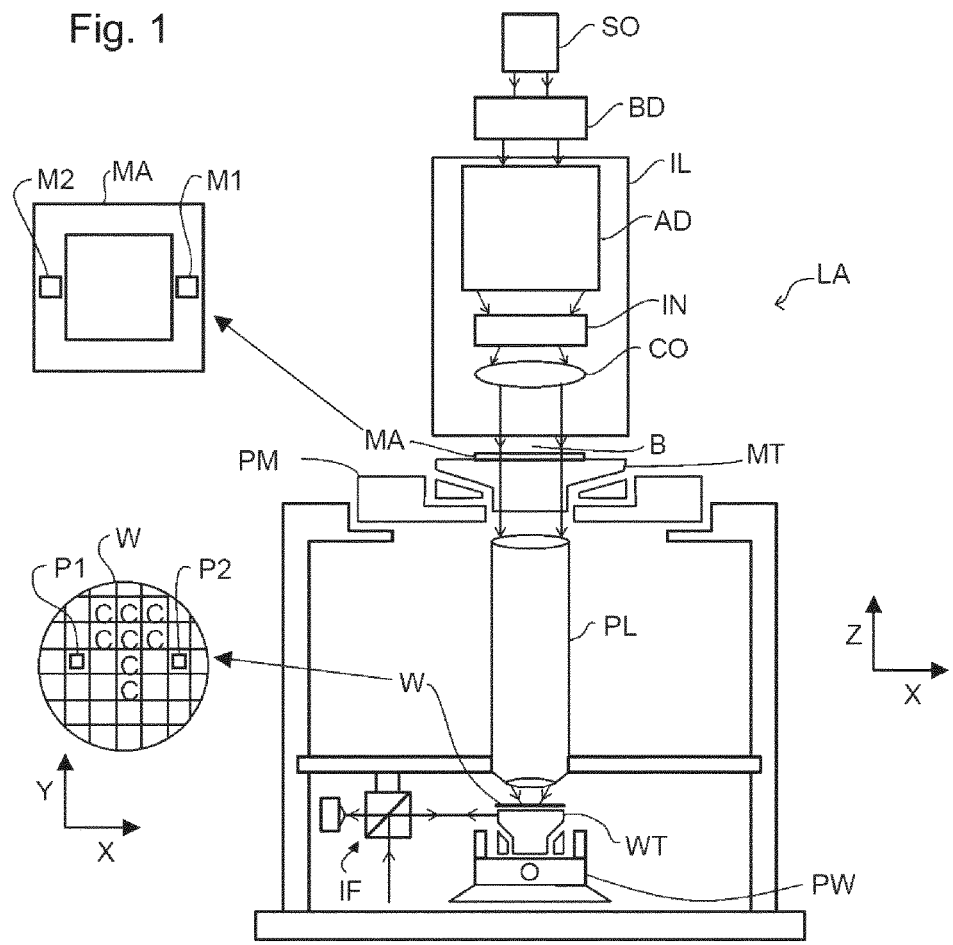
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present example environments in which embodiments of the present invention may be implemented.

FIG. 1 schematically depicts a lithographic apparatus. The apparatus comprises: an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist-coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is—reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
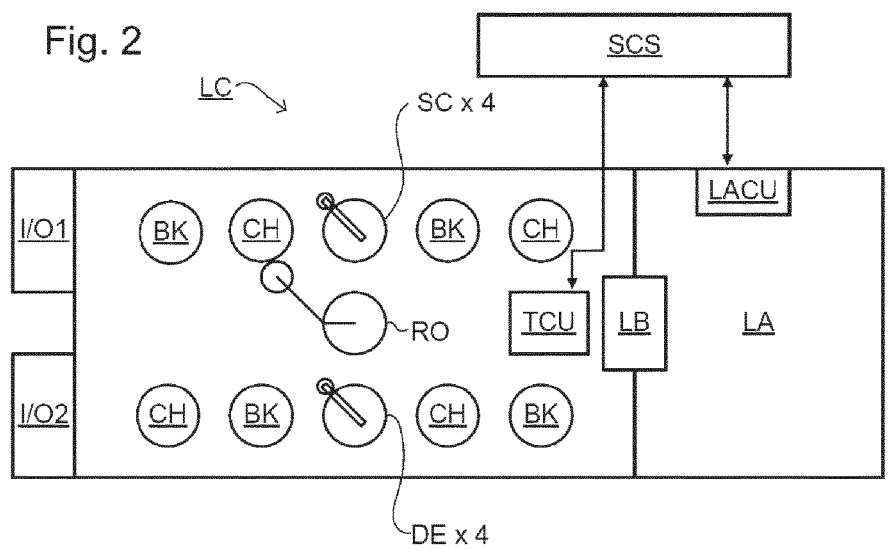
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
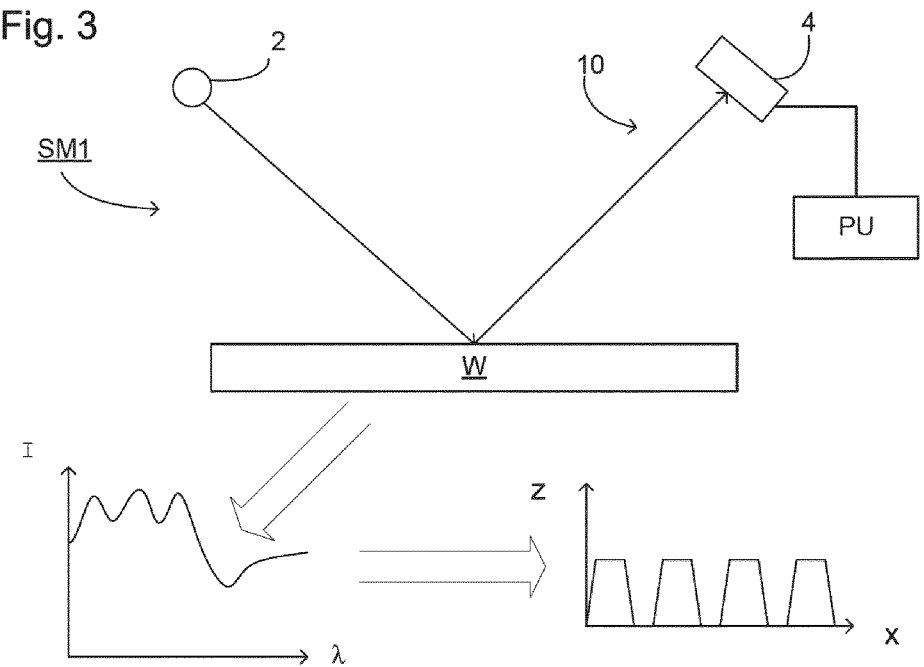
FIG. 3 depicts a first scatterometer.

FIG. 3 depicts a scatterometer which may be used in an embodiment of the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., conventionally by Rigorous Coupled Wave Analysis (RCWA) and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
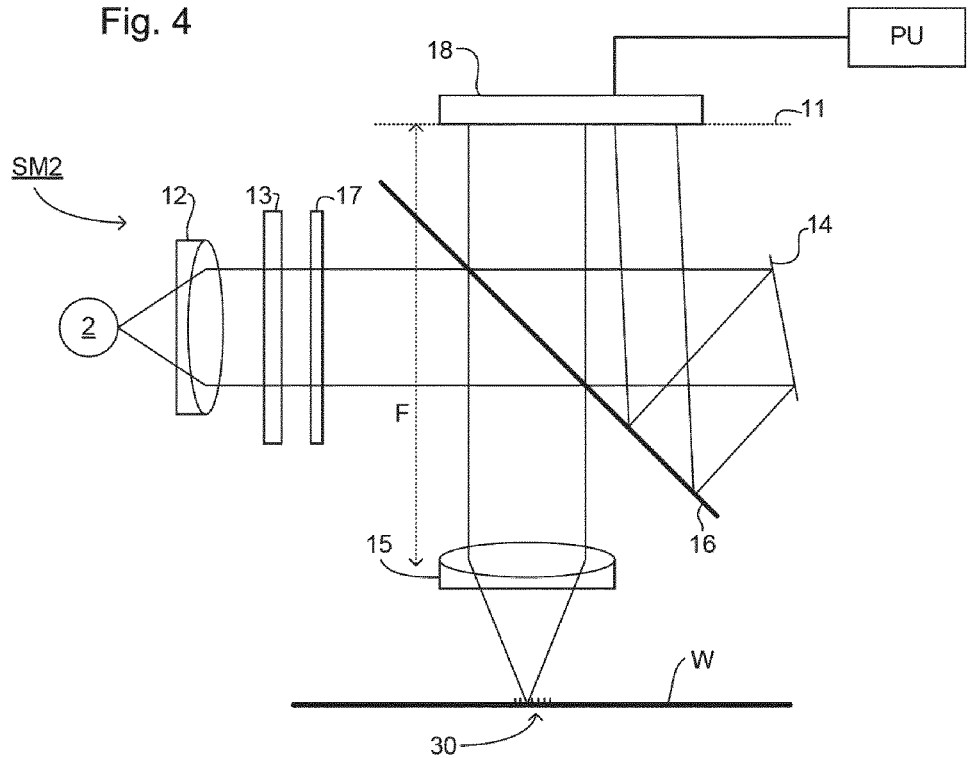
FIG. 4 depicts a second scatterometer.

Another scatterometer that may be used in an embodiment of the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least $2\Delta\lambda$ (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

Modelling

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Using one of the scatterometers described above in combination with modeling of a target structure such as the target 30 and its diffraction properties, measurement of the shape and other parameters of the structure can be performed in a number of ways. In a first type of process, represented by FIG. 5, a diffraction pattern based on a first estimate of the target shape (a first candidate structure) is calculated and compared with the observed diffraction pattern. Parameters of the model are then varied systematically and the diffraction re-calculated in a series of iterations, to generate new candidate structures and so arrive at a best fit. In a second type of process, represented by FIG. 6, diffraction spectra for many different candidate structures are calculated in advance to create a 'library' of diffraction spectra. Then the diffraction pattern observed from the measurement target is compared with the library of calculated spectra to find a best fit. Both methods can be used together: a coarse fit can be obtained from a library, followed by an iterative process to find a best fit.

Figure 5:
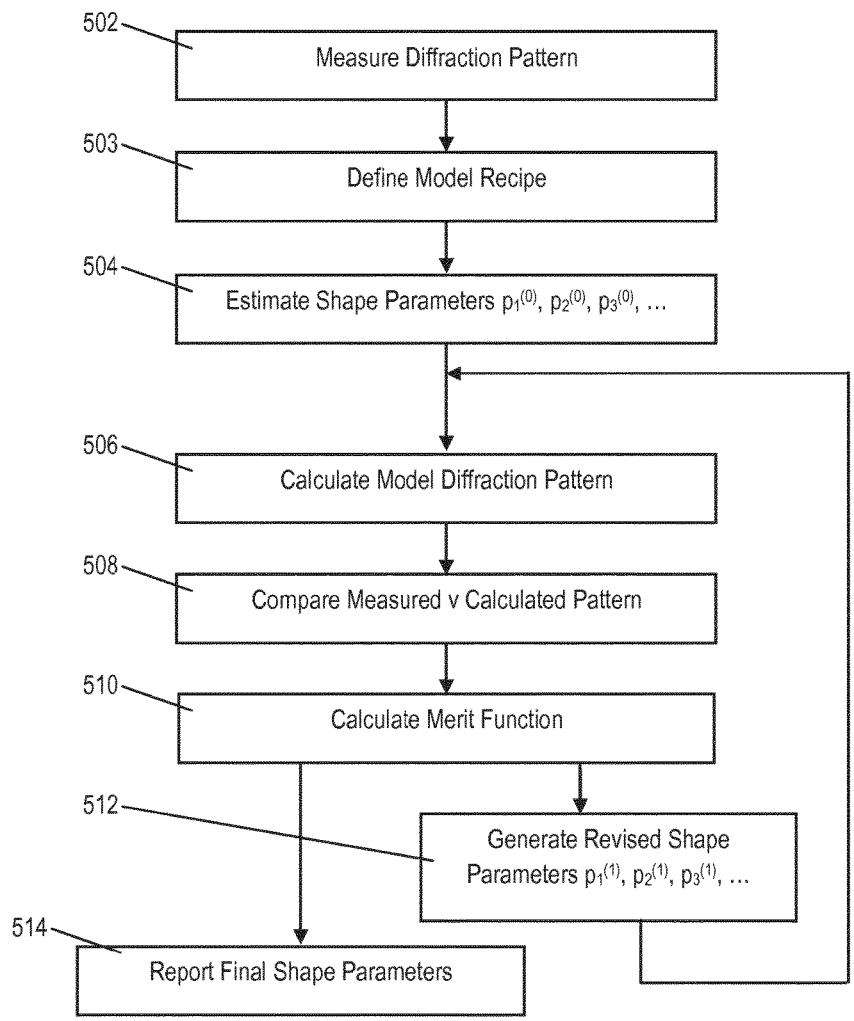
FIG. 5 depicts a first example process using an embodiment of the invention for reconstruction of a structure from scatterometer measurements.

Referring to FIG. 5 in more detail, the way the measurement of the target shape and/or material properties is carried out will be described in summary. The target will be assumed for this description to be a 1-dimensional (1-D) structure. In practice it may be 2-dimensional, and the processing will be adapted accordingly.

In step 502, the diffraction pattern of the actual target on the substrate is measured using a scatterometer such as those described above. This measured diffraction pattern is forwarded to a calculation system such as a computer. The calculation system may be the processing unit PU referred to above, or it may be a separate apparatus.

In step 503, a 'model recipe' is established which defines a parameterized model of the target structure in terms of a number of parameters $p_i$ ($p_1$, $p_2$, $p_3$ and so on). These parameters may represent for example, in a 1D periodic structure, the angle of a side wall, the height or depth of a feature, the width of the feature. Properties of the target material and underlying layers are also represented by parameters such as refractive index (at a particular wavelength present in the scatterometry radiation beam). Specific examples will be given below. Importantly, while a target structure may be defined by dozens of parameters describing its shape and material properties, the model recipe will define many of these to have fixed values, while others are to be variable or 'floating' parameters for the purpose of the following process steps. Further below we describe the process by which the choice between fixed and floating parameters is made. Moreover, we shall introduce ways in which parameters can be permitted to vary without being fully independent floating parameters. For the purposes of describing FIG. 5, only the variable parameters are considered as parameters $p_i$.

In step 504: A model target shape is estimated by setting initial values $p_i^{(0)}$ for the floating parameters (i.e. $p_1^{(0)}$, $p_2^{(0)}$, $p_3^{(0)}$ and so on). Each floating parameter will be generated within certain predetermined ranges, as defined in the recipe.

In step 506, the parameters representing the estimated shape, together with the optical properties of the different elements of the model, are used to calculate the scattering properties, for example using a rigorous optical diffraction method such as RCWA or any other solver of Maxwell equations. This gives an estimated or model diffraction pattern of the estimated target shape.

In steps 508 and 510, the measured diffraction pattern and the model diffraction pattern are then compared and their similarities and differences are used to calculate a "merit function" for the model target shape.

In step 512, assuming that the merit function indicates that the model needs to be improved before it represents accurately the actual target shape, new parameters $p_1^{(1)}$, $p_2^{(1)}$, $p_3^{(1)}$, etc. are estimated and fed back iteratively into step 506. Steps 506-512 are repeated.

In order to assist the search, the calculations in step 506 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

In step 514, when the merit function indicates that this iterative process has converged on a solution with a desired accuracy, the currently estimated parameters are reported as the measurement of the actual target structure.

The computation time of this iterative process is largely determined by the forward diffraction model used, i.e. the calculation of the estimated model diffraction pattern using a rigorous optical diffraction theory from the estimated target structure. If more parameters are required, then there are more degrees of freedom. The calculation time increases in principle with the power of the number of degrees of freedom.

The estimated or model diffraction pattern calculated at 506 can be expressed in various forms. Comparisons are simplified if the calculated pattern is expressed in the same form as the measured pattern generated in step 510. For example, a modeled spectrum can be compared easily with a spectrum measured by the apparatus of FIG. 3; a modeled pupil pattern can be compared easily with a pupil pattern measured by the apparatus of FIG. 4.

Throughout this description from FIG. 5 onward, the term 'diffraction pattern' will be used, on the assumption that the scatterometer of FIG. 4 is used. The skilled person can readily adapt the teaching to different types of scatterometer, or even other types of measurement instrument.

Figure 6:
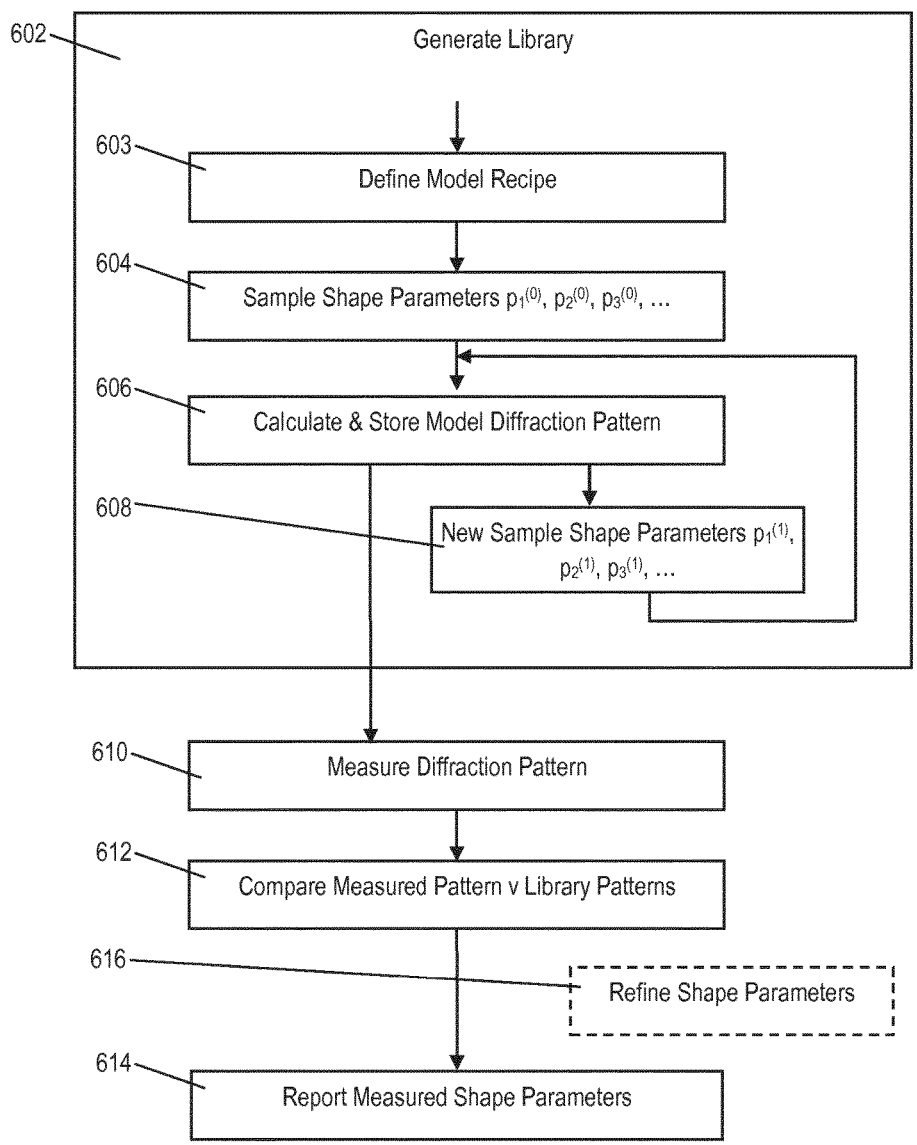
FIG. 6 depicts a second example process using an embodiment of the invention for reconstruction of a structure from scatterometer measurements.

FIG. 6 illustrates an alternative example process in which plurality of model diffraction patterns for different estimated target shapes (candidate structures) are calculated in advance and stored in a library for comparison with a real measurement. The underlying principles and terminology are the same as for the process of FIG. 5. The steps of the FIG. 6 process are:

In step 602, the process of generating the library is performed. A separate library may be generated for each type of target structure. The library may be generated by a user of the measurement apparatus according to need, or may be pre-generated by a supplier of the apparatus.

In step 603, a 'model recipe' is established which defines a parameterized model of the target structure in terms of a number of parameters $p_i$ ($p_1$, $p_2$, $p_3$ and so on). Considerations are similar to those in step 503 of the iterative process.

In step 604, a first set of parameters $p_1^{(0)}$, $p_2^{(0)}$, $p_3^{(0)}$, etc. is generated, for example by generating random values of all the parameters, each within its expected range of values.

In step 606, a model diffraction pattern is calculated and stored in a library, representing the diffraction pattern expected from a target shape represented by the parameters.

In step 608, a new set of parameters $p_1^{(1)}$, $p_2^{(1)}$, $p_3^{(1)}$, etc. is generated. Steps 606-608 are repeated tens, hundreds or even thousands of times, until the library which comprises all the stored modeled diffraction patterns is judged sufficiently complete. Each stored pattern represents a sample point in the multi-dimensional parameter space. The samples in the library should populate the sample space with a sufficient density that any real diffraction pattern will be sufficiently closely represented.

In step 610, after the library is generated (though it could be before), the real target 30 is placed in the scatterometer and its diffraction pattern is measured.

In step 612, the measured pattern is compared with the modeled patterns stored in the library to find the best matching pattern. The comparison may be made with every sample in the library, or a more systematic searching strategy may be employed, to reduce computational burden.

In step 614, if a match is found then the estimated target shape used to generate the matching library pattern can be determined to be the approximate object structure. The shape parameters corresponding to the matching sample are output as the measured shape parameters. The matching process may be performed directly on the model diffraction signals, or it may be performed on substitute models which are optimized for fast evaluation.

In step 616, optionally, the nearest matching sample is used as a starting point, and a refinement process is used to obtain the final parameters for reporting. This refinement process may comprise an iterative process very similar to that shown in FIG. 5, for example.

Whether refining step 616 is needed or not is a matter of choice for the implementer. If the library is very densely sampled, then iterative refinement may not be needed because a good match will always be found. On the other hand, such a library might too large for practical use. A practical solution is thus to use a library search for a coarse set of parameters, followed by one or more iterations using the merit function to determine a more accurate set of parameters to report the parameters of the target substrate with a desired accuracy. Where additional iterations are performed, it would be an option to add the calculated diffraction patterns and associated refined parameter sets as new entries in the library. In this way, a library can be used initially which is based on a relatively small amount of computational effort, but which builds into a larger library using the computational effort of the refining step 616. Whichever scheme is used, a further refinement of the value of one or more of the reported variable parameters can also be obtained based upon the goodness of the matches of multiple candidate structures. For example, the parameter values finally reported may be produced by interpolating between parameter values of two or more candidate structures, assuming both or all of those candidate structures have a high matching score.

The computation time of this iterative process is largely determined by the forward diffraction model at steps 506 and 606, i.e. the calculation of the estimated model diffraction pattern using a rigorous optical diffraction theory from the estimated target shape.

For CD reconstruction of 2D-periodic structures RCWA is commonly used in the forward diffraction model, while the Differential Method, the Volume Integral Method (VIM), Finite-difference time-domain (FDTD), and Finite element method (FFM) have also been reported. A Fourier series expansion as for example used in RCWA and the Differential Method can also be used to analyze aperiodic structures by employing perfectly matched layers (PMLs), or other types of absorbing boundary conditions to mimic radiation towards infinity, near the boundary of the unit cell on which the Fourier expansions are used.

Volume Integral Method

One of the major problems of RCWA is that it requires a large amount of central processing unit (CPU) time and memory for 2D periodic structures, since a sequence of eigenvalue/eigenvector problems need to be solved and concatenated. For FDTD and FEM, CPU time is typically also too high.

Known Volume Integral Methods (as disclosed in U.S. Pat. No. 6,867,866 B1 and U.S. Pat. No. 7,038,850 B2) are based either on fully spatial discretization schemes that exhibit slow convergence with respect to mesh refinement or on spectral discretization schemes that exhibit poor convergence with respect to an increasing number of harmonics. As an alternative, a spectral discretization scheme that incorporates a heuristic method to improve the convergence was proposed.

The linear system that has to be solved for VIM is much larger compared to RCWA, but if it is solved in an iterative way, only the matrix-vector product is needed together with the storage of several vectors. Therefore, the memory usage is typically much lower than for RCWA. The potential bottleneck is the speed of the matrix-vector product itself. If the Li rules, also known as the Fourier factorization rules, were to be applied in VIM, then the matrix-vector product would be much slower, due to the presence of several inverse sub-matrices. Alternatively, the Li rules can be ignored and FFTs can be used to arrive at a fast matrix-vector product, but the problem of poor convergence remains.

Figure 7:
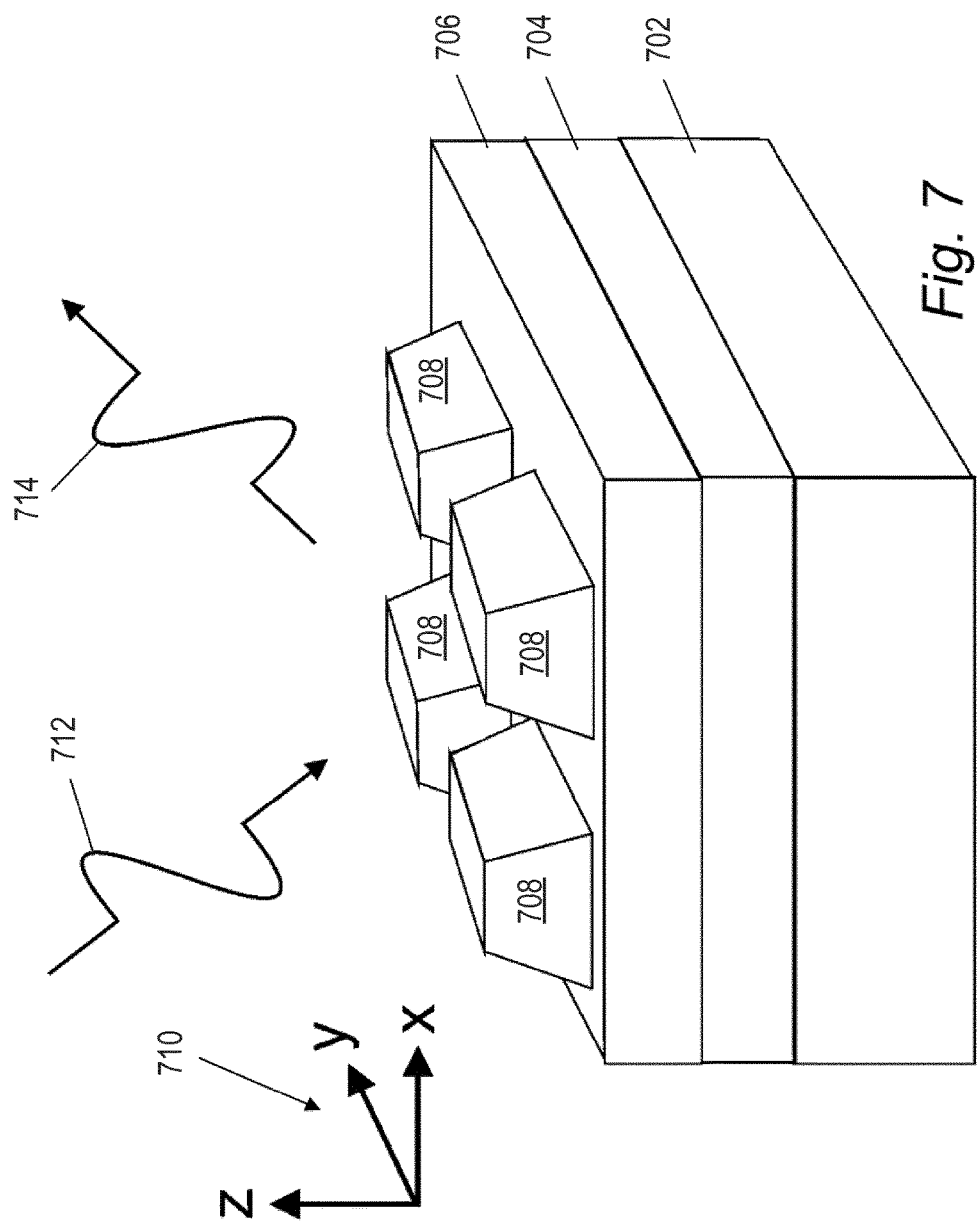
FIG. 7 depicts the scattering geometry that may be reconstructed in accordance with an embodiment of the present invention.

FIG. 7 illustrates schematically the scattering geometry that may be reconstructed in accordance with an embodiment of the present invention. A substrate 702 is the lower part of a medium layered in the z direction. Other layers 704 and 706 are shown. A two dimensional grating 708 that is periodic in x and y is shown on top of the layered medium. The x, y and z axes are also shown 710. An incident field 712 interacts with and is scattered by the structure 702 to 708 resulting in a reflected field 714. Thus the structure is periodic in at least one direction, x, y, and includes materials of differing properties such as to cause a discontinuity in an electromagnetic field, $E^{tot}$, that comprises a total of incident, $E^{inc}$, and scattered, $E^s$, electromagnetic field components at a material boundary between the differing materials.

Figure 9:
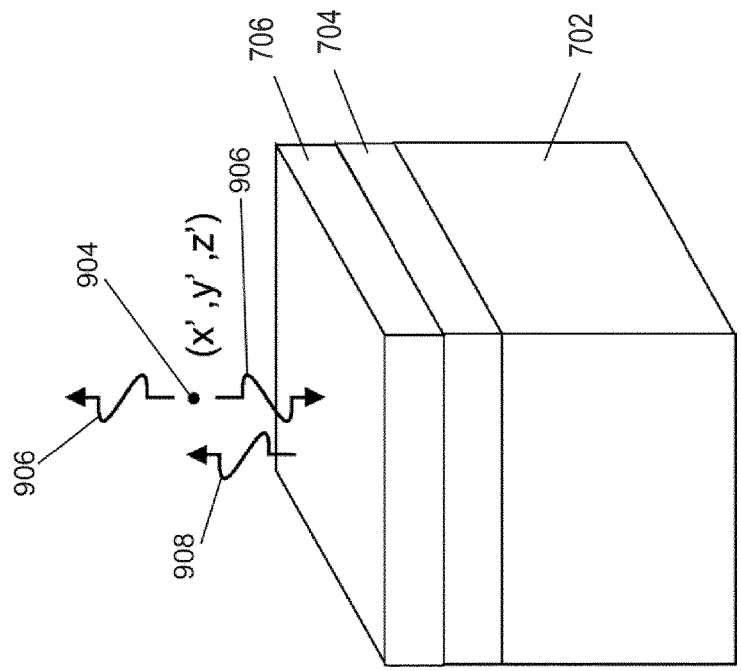
FIG. 9 illustrates use of a Green's function to calculate the interaction of the incident field with the layered medium.
Figure 8:
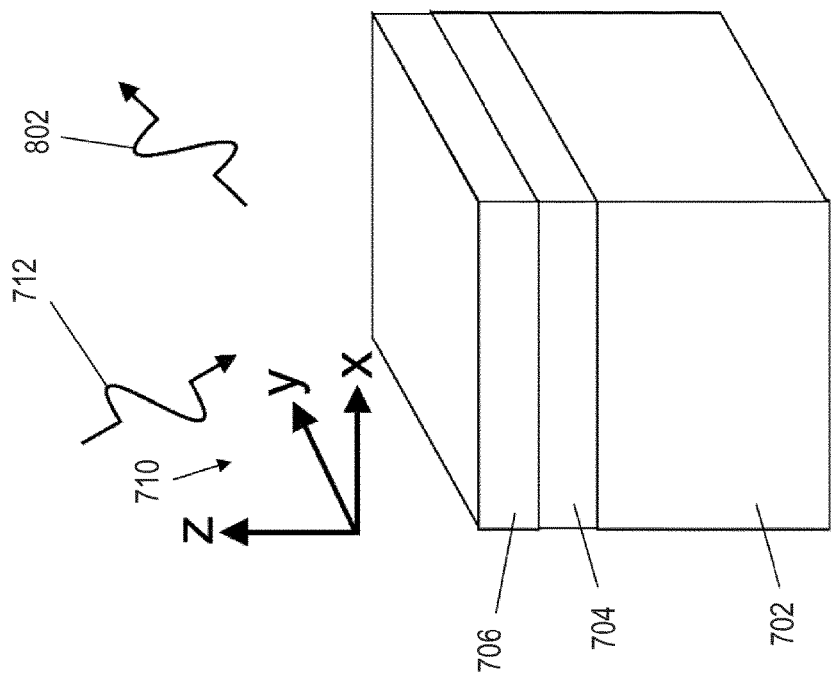
FIG. 8 depicts the structure of the background.

FIG. 8 shows the structure of the background and FIG. 9 schematically illustrates the Green's function that may be used to calculate the interaction of the incident field with the layered medium. In FIGS. 8 and 9, the layered medium 702 to 706 corresponds to the same structure as in FIG. 7. In FIG. 8, the x, y and z axes are also shown 710 along with the incident field 712. A directly reflected field 802 is also shown. With reference to FIG. 9, the point source (x', y', z') 904 represents the Green's function interaction with the background that generates a field 906. In this case because the point source 904 is above the top layer 706 there is only one background reflection 908 from the top interface of 706 with the surrounding medium. If the point source is within the layered medium then there will be background reflections in both up and down directions (not shown).

The VIM formula to be solved is $$E^{inc}(x,y,z) = E^{tot}(x,y,z) - \iiint \overline{G}(x,x',y,y',z,z') J^c(x',y',z') dx'dy'dz' \quad (0.1)$$

$$J^c(x',y',z') = \chi(x',y',z') E^{tot}(x',y',z') \quad (0.2)$$

In this equation, the incident field $E^{inc}$ is a known function of angle of incidence, polarization and amplitude, $E^{tot}$ is the total electric field that is unknown and for which the solution is calculated, $J^c$ is the contrast current density, $\overline{G}$ is the Green's function (a 3×3 matrix), $\chi$ is the contrast function given by $j\omega(\in(x,y,z,)-\in_b(z))$, where $\in$ is the permittivity of the structure and $\in_b$ is the permittivity of the background medium. $\chi$ is zero outside the gratings.

The Green's function $\overline{G}(x,x',y,y',z,z')$ is known and computable for the layered medium including 702 to 706. The Green's function shows a convolution and/or modal decomposition ($m_1$, $m_2$) in the xy plane and the dominant computation burden along the z axis in $\overline{G}$ are convolutions.

For discretization, the total electric field is expanded in Bloch/Floquet modes in the xy plane. Multiplication with $\chi$ becomes: (a) discrete convolution in the xy plane (2D FFT); and (b) product in z. The Green's function interaction in the xy plane is an interaction per mode. The Green's function interaction in z that corresponds to a homogeneous background medium is a convolution that may be performed with one-dimensional (1D) FFTs with a complexity O(N log N). Alternatively, but not shown in the figure, the Green's function interaction in z can be computed by exploiting its semi-separability property via an upward and downward recurrence relation in z, with a complexity O(N). The contributions from the reflections of the layered medium above and below the grating can be added by reusing a part of the result that has already been computed as part of the interaction for a homogeneous background medium.

The number of modes in xy is $M_1M_2$ and the number of samples in z is N.

The efficient matrix-vector product has a complexity $O(M_1M_2N \log(M_1M_2N))$ and the storage complexity is $O(M_1M_2N)$.

Figure 10:
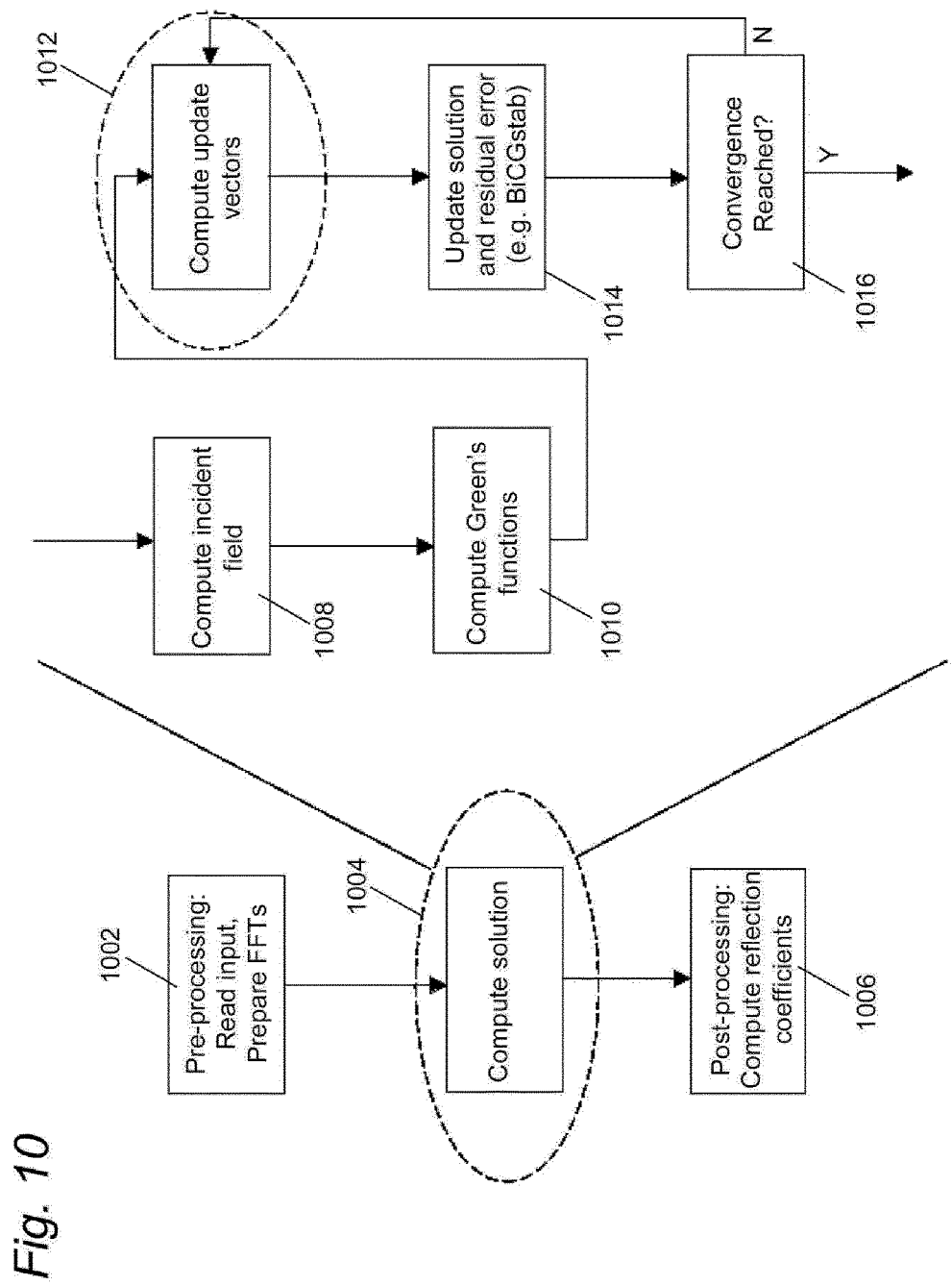
FIG. 10 is a flow chart of the high level method of solving the linear system corresponding to the VIM formula for the contrast current density, the electric field, or a vector field that is composed of a linear combination of the electric field and the electric flux density.

The VIM solution method for Ax=b is performed using an iterative solver based on a Krylov subspace method, e.g., BiCGstab(l) (Stabilized BiConjugate Gradient method), which typically has the steps:
Define residual error as $r_n=b-Ax_n$
Compute update vector(s) $v_n$ via residual error
Update solution: $x_{n+1}=x_n+\alpha_n v_n$
Update residual error $r_{n+1}=r_n-\alpha_n Av_n$ FIG. 10 is a flow chart of the high level method of solving the linear system corresponding to the VIM formula. This is a method of calculating electromagnetic scattering properties of a structure, by numerically solving a volume integral. At the highest level the first step is pre-processing 1002, including reading the input and preparing FFTs. The next step is to compute the solution 1004. Finally, post-processing 1006 is performed in which reflection coefficients are computed. Step 1004 includes various steps also shown at the right hand side of FIG. 10. These steps are computing the incident field 1008, computing the Green's Functions 1010, computing the update vectors 1012, updating the solution and residual error (e.g., using BiCGstab) 1014 and testing to see if convergence is reached 1016. If convergence is not reached control loops back to step 1012 that is the computation of the update vectors.

Figure 11:
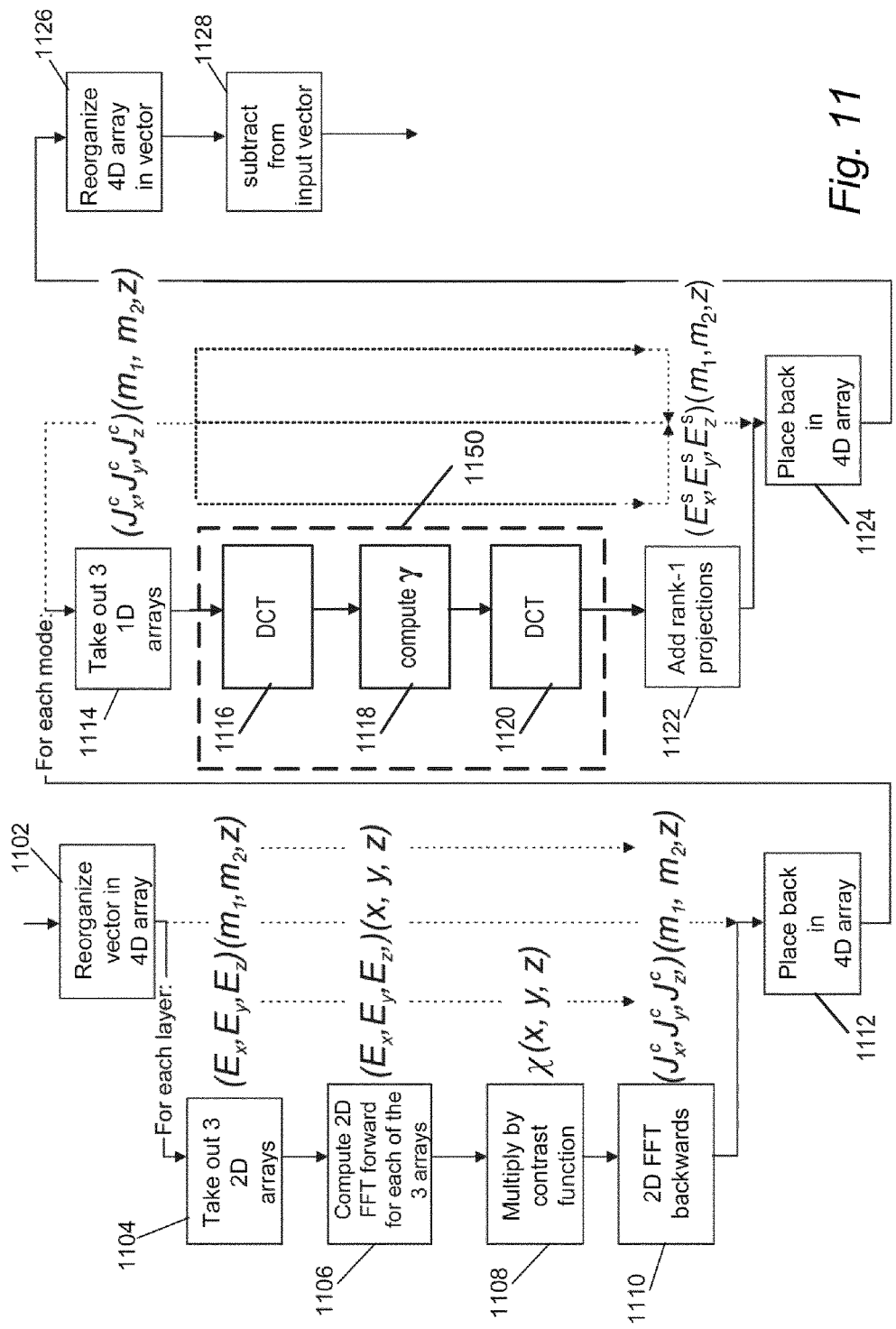
FIG. 11 is a flow chart of the computation of update vectors using the VIM formula for the electric field, in accordance with an embodiment of the present invention.

FIG. 11 illustrates the steps in computing update vectors corresponding to step 1012 of FIG. 10 using a volume integral method, in accordance with an embodiment of the present invention, which is a method of calculating electromagnetic scattering properties of a structure, by numerically solving a volume integral equation for an electric field, E.

Step 1102 is reorganising the vector in a four-dimensional (4D) array. In this array the first dimension has three elements $E_x$, $E_y$, and $E_z$. The second dimension has elements for all values of $m_1$. The third dimension has elements for all values of $m_2$. The fourth dimension has elements for each value of z. Thus the 4D array stores the spectral (in the xy plane) representation of the total electric field $(E_x,E_y,E_z)(m_2,m_2,z)$. The three parallel dotted arrows descending from step 1102 in FIG. 11 correspond to the processing of three 2D arrays, one each for $E_x$, $E_y$ and $E_z$ respectively, by steps 1104 to 1110 carried out for each layer, z. These steps perform the convolution of the spectral (in the xy plane) representation of the electric field $(E_x,E_y,E_z)(m_2,m_2,z)$ with the material properties to calculate the spectral (in the xy plane) representation of the contrast current density $(J_x^c,J_y^c,J_z^c)(m_1,m_2,z)$ corresponding to Equation (0.2) below. In detail, step 1104 involves taking out the three 2D arrays (the two dimensions being for $m_1$ and $m_2$). In step 1106 a 2D FFT is computed forward for each of the three arrays into the spatial domain. In step 1108 each of the three arrays is multiplied by the spatial representation of the contrast function x(x,y,z) that is filtered by the truncation of the Fourier representation. The convolution is completed in step 1110 with the 2D FFT backwards into the spectral (in the xy plane) domain yielding the spectral contrast current density $(J_x^c,J_y^c,J_z^c)(m_1,m_2,$ z). In step 1112 the calculated spectral contrast current density is placed back into the 4D array.

Then for each mode (i.e. for all sample points in z, at the same time), steps 1114 to 1122 are performed. The three dotted parallel arrows descending from beside step 1116 correspond to computing an integral term, which is the background interaction with the contrast current density that has itself arisen from the total electric field's interaction with the structure. This has been known to be performed by a convolution of $(J_x^c, J_y^c, J_z^c)(m_1, m_2, z)$ with the spatial (with respect to the z direction) Green's function, using a multiplication in the spectral domain (with respect to the z direction). However, in accordance with an embodiment of the present invention, integration of a pseudo-spectral polynomial expansion multiplied by a 1D Green's function is performed by solving a regularized linear system of equations. Two regularized systems may be solved: one for the upward integration and one for the downward integration. Two uncoupled systems can be brought under one matrix equation that is twice as large. The linear system of equations may be regularized by modifying the linear system to compensate for expansion coefficients prone to conditioning-related errors by defining an extended regularized expansion coefficient vector. Regularizing the linear system of equations may include generating a function, F(k), at sample points in the orthogonal direction, the function comprising expansion coefficients prone to conditioning-related errors, such that the modifying of the linear system compensates for the function, F(k).

In detail, in step 1114 the spectral contrast current density $(J_x^c, J_y^c, J_z^c)(m_1, m_2, z)$ is taken out as three 1D arrays for each of x, y, and z. Steps 1116 to 1120 involve solving 1118 the regularized linear system of equations between first and second discrete transformation steps 1116 and 1120 to values of the regularized expansion coefficient vector, γ. The dashed box 1150 including steps 1116 to 1120 corresponds to the steps described with reference to FIGS. 17A and 17B, which provide a more detailed description. In step 1122 background reflections (see 908 in FIG. 9) in the spatial domain with respect to z are added. This separation of the background reflections from the Green's function is a conventional technique and the step may be performed by adding rank-1 projections as will be appreciated by one skilled in the art. As each mode is processed then the update vectors for the total electric field, $(E_x, E_y, E_z)(m_2, m_2, z)$, thus calculated are placed back into the 4D array in step 1124.

The next step is reorganizing the 4D array in a vector 1126, which is different from step 1102 "reorganizing the vector in a 4D array", in that it is the reverse operation: each one-dimensional index is uniquely related to a four-dimensional index. Finally in step 1128 the vector output from step 1126 is subtracted from the input vector, corresponding to the subtraction in the right-hand side of Equation (0.1). The input vector is the vector that enters at step 1102 in FIG. 11 and contains $(E_x, E_y, E_z)(m_1, m_2, z)$.

A problem with the method described in FIG. 11 is that it leads to poor convergence. This poor convergence is caused by concurrent jumps in permittivity and contrast current density for the truncated Fourier-space representation. As discussed above, in the VIM method the Li inverse rule is not suitable for overcoming the convergence problem because in VIM the complexity of the inverse rule leads to a very large computational burden because of the very large number of inverse operations that are needed in the VIM numerical solution. US patent application publication no. US2011/0218789 A1, which is incorporated herein by reference, disclosed a way of overcoming convergence problems caused by concurrent jumps without resorting to use of the inverse rule as described by Li. By avoiding the inverse rule, the approach of US2011/0218789 A1 does not sacrifice the efficiency of the matrix-vector product that is required for solving the linear system in an iterative manner in the VIM approach.

US2011/0218789 A1 disclosed that improved convergence in the volume-integral method (VIM) of calculating electromagnetic scattering properties of a structure is achieved by numerically solving a volume integral equation for a vector field, F, rather than the electric field, E. The vector field, F, may be related to the electric field, E, by a change of basis, and may be continuous at material boundaries where the electric field, E, has discontinuities. Convolutions of the vector field, F, are performed using convolution operators according the finite Laurent rule (that operate according to a finite discrete convolution), which allow for efficient matrix-vector products via 1D and/or 2D FFTs (Fast Fourier Transforms). An invertible convolution-and-change-of-basis operator, C, is configured to transform the vector field, F, to the electric field, E, by performing a change of basis according to material and geometric properties of the periodic structure.

After solving the volume integral for the vector field, F, an additional post-processing step may be used to obtain the electric field, E, from the vector field, F.

The vector field, F, may be constructed from a combination of field components of the electric field, E, and the electric flux density, D, by using a normal-vector field, n, to filter out continuous components.

The improved volume-integral method may be incorporated into a forward diffraction model in metrology tools for reconstructing an approximate structure of an object, for example to assess critical dimensions (CD) performance of a lithographic apparatus.

Figure 12:
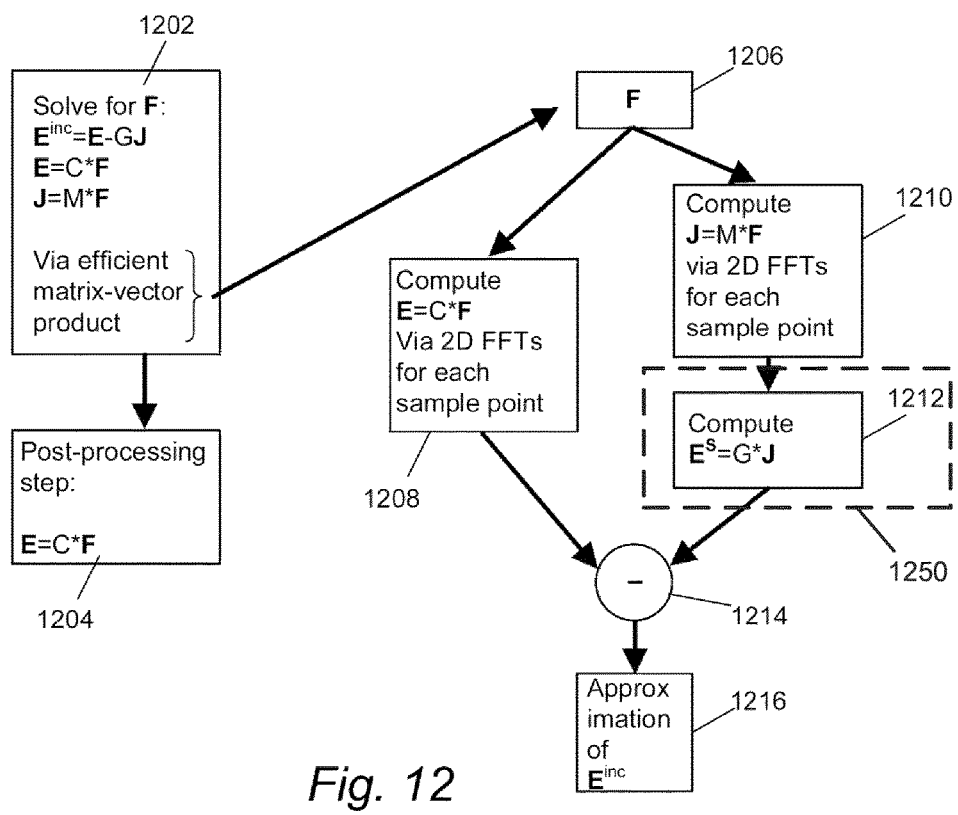
FIG. 12 depicts an embodiment of the present invention using a continuous vector field to numerically solve the VIM formula.

FIG. 12 illustrates an embodiment of the present invention using a continuous vector field to numerically solve the VIM formula. This involves numerically solving a volume integral equation for a vector field, F, that is related to the electric field, E, by a change of basis, the vector field, F, being continuous at one or more material boundaries, so as to determine an approximate solution of the vector field, F. The vector field, F, is represented by at least one finite Fourier series with respect to at least one direction, x, y, and the step of numerically solving the volume integral equation comprises determining a component of the electric field, E, by convolution of the vector field, F, with a convolution-and-change-of-basis operator, C, and determining a current density, J, by convolution of the vector field, F, with a convolution operator, M. The convolution-and-change-of-basis operator, C, is invertible and comprises material and geometric properties of the structure in at least one direction x, y and is configured to transform the vector field, F, to the electric field, E, by performing a change of basis according to the material and geometric properties. The convolution operator, M, comprises material and geometric properties of the structure in the at least one direction, x, y. The current density, J, may be a contrast current density and is represented by at least one finite Fourier series with respect to the at least one direction, x, y. The convolutions are performed using a transformation such as one selected from a set comprising a fast Fourier transform (FFT) and number-theoretic transform (NTT). The convolution-and-change-of-basis operator, C, and the convolution operator, M, operate according to a finite discrete convolution, so as to produce a finite result.

FIG. 12 shows the step 1202 of solving the VIM system for an intermediate vector field, F, with a post-processing step 1204 to obtain a total electric field, E, by convolution of the approximate solution of the vector field, F, with the convolution-and-change-of-basis operator, C. The convolution may be performed using a transformation such as one selected from a set comprising a fast Fourier transform (FFT) and number-theoretic transform (NTT). FIG. 12 also shows at the right hand side a schematic illustration of performing an efficient matrix-vector product 1206 to 1216 to solve the VIM system iteratively. This starts with an intermediate vector field, F, in step 1206. The first time that F is set up, it can be started from zero. After that initial step, the estimates of F are guided by the iterative solver and the residual. Next the total electric field, E, is computed 1208 using the convolution of a convolution-and-change-of-basis operator, C, with the intermediate vector field, F, via 2D FFTs for each sample point in the z direction. The convolution-and-change-of-basis operator, C, is configured to transform the basis of the intermediate vector field, F, to the basis of the total electric field, E. Also, the contrast current density, J, is computed in step 1210 using a convolution of a material convolution operator, M, with the intermediate vector field, F. Step 1210 is performed for each sample point in z with the convolution being performed via 2D FFTs. In step 1212 the interaction and rank-1 projections between the Green's function, G, and the contrast current density, J, are computed to yield the scattered electric field, $E^s$. Operation 1214 subtracts the two computed results $E^s$ from E to obtain an approximation of $E^{inc}$ 1216. Because steps 1206 to 1216 produce update vectors then the post-processing step 1204 is used to produce the final value of the total electric field, E.

Rather than a separate post-processing step 1204 the sum of all the update vectors may be recorded at step 1208 in order to calculate the total electric field, E. However, that approach increases the storage requirements of the method, whereas the post-processing step 1204 is not costly in storage or processing time, compared to the iterative steps 1206 to 1216.

Thus, on the left-hand side of FIG. 12, the linear system corresponding to the spectral VIM is specified. The linear system is solved via an iterative solver and the efficient matrix-vector product of the VIM that is specified in the flow chart on the right-hand side of FIG. 12. An embodiment of the present invention concerns the block 1212 "Compute $E^s=-G*J$" on the right-hand side of the matrix-vector product flow chart. This block evaluates the scattered electric field $E^s$ due to the contrast current density J. In accordance with an embodiment of the present invention, in this block, integration of a pseudo-spectral polynomial expansion multiplied by a 1D Green's function is performed by solving a regularized linear system of equations. In the same way as discussed with reference to FIG. 11, two regularized systems may be solved: one for the upward integration and one for the downward integration. Two uncoupled systems can be brought under one matrix equation that is twice as large. The linear system of equations may be regularized by modifying the linear system to compensate for expansion coefficients prone to conditioning-related errors by defining an extended regularized expansion coefficient vector. Regularizing the linear system of equations may include generating a function, F(k), at sample points in the orthogonal direction, the function comprising expansion coefficients prone to conditioning-related errors, such that the modifying of the linear system compensates for the function, F(k).

The computation of this part of the matrix-vector product is based on the closed-form analytical integration of a Chebyshev expansion for the quantity J, sampled on a (non-uniform) Chebyshev grid, multiplied by the 1D Green's function for the 1D Helmholtz equations. Via a discrete cosine transform (DCT) for the closed Chebyshev rules (i.e. DCT type I), the sampled values of J are converted into coefficients for the Chebyshev expansion. Subsequently, the expansion is integrated, by solving an analytically regularized linear system, where the analytic regularization described herein is the first for an application of computing Fourier integrals. The latter step results in a set of coefficients for a new Chebyshev expansion that represents the result after integration with the Green's function. As a final step, the expansion is evaluated on the same non-uniform Chebyshev grid. The dashed box 1250 corresponds to the steps enclosed by dashed box 1350 described with reference to FIG. 13 and the steps described with reference to FIGS. 17A and 17B.

A distinct difference with previous approaches is that embodiments described herein may address not just a single 1D integral equation, but a whole system of 1D integral equations or a single integral, for which coupling occurs due to field-material interactions that are evaluated on the same grid in the longitudinal direction. The longitudinal direction is the "aperiodic" or "orthogonal" direction (for example z) orthogonal to the lateral directions (for example x, y) in which the structure is periodic. Embodiments described herein address both efficiency and stability within one algorithm for all modes at the same time.

Figure 13:
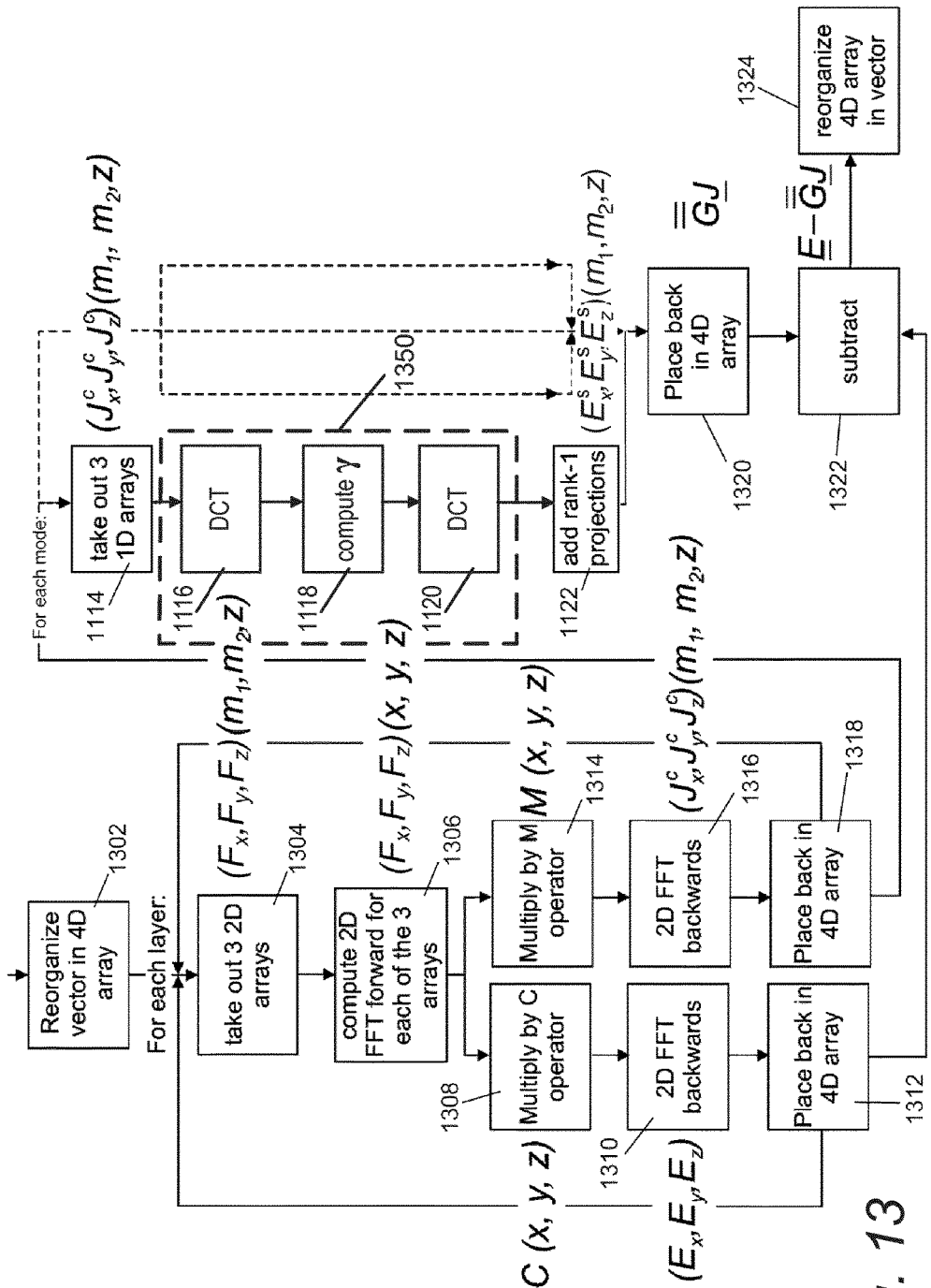
FIG. 13 is a flow chart of the computation of update vectors in accordance with an embodiment of the present invention.

FIG. 13 is a flow chart of the computation of update vectors in accordance with an embodiment of the present invention, based on the disclosure of US2011/0218789 A1. The flow chart of FIG. 13 corresponds to the right hand side (steps 1206 to 1216) of FIG. 12.

In step 1302 the vector is reorganised in a 4D array. Then for each sample point in z, steps 1304 to 1318 are performed. In step 1304 three 2D arrays are taken out of the 4D array. These three 2D arrays $(F_{t1},F_{t2},F_n)(m_1,m_2,z)$ correspond respectively to the two tangential components $F_{t1}$, $F_{t2}$ and the normal component $F_n$ of the continuous vector field, F, each having the 2 dimensions corresponding to $m_1$ and $m_2$. Thus the vector field, F, is constructed from a combination of field components of the electromagnetic field, E, and a corresponding electromagnetic flux density, D, by using a normal-vector field, n, to filter out continuous components of the electromagnetic field, E, tangential to the at least one material boundary and also to filter out the continuous components of the electromagnetic flux density, D, normal to the at least one material boundary. In 1306 the convolution of the spectral continuous vector field, represented by $(F_{t1},F_{t2},F_n)(m_1,m_2,z)$ begins with the computation in step 1306 of the 2D FFT forward into the spatial domain for each of the three arrays, represented by $(F_{t1},F_{t2},F_n)(x,y,z)$. In step 1308 the Fourier transform $(F_{t1},F_{t2},F_n)(x,y,z)$ obtained from step 1306 is multiplied in the spatial domain by the spatial multiplication operator C(x,y,z). In step 1310 the product obtained in step 1308 is transformed into the spectral domain by a 2D FFT backwards. The spectral total electric field, $(E_x,E_y,E_z)$, is then placed back in the 4D array at step 1312. Furthermore, a copy is fed forward to the subtract operation 1322 discussed below.

In step 1314 the Fourier transform $(F_{t1},F_{t2},F_n)(x,y,z)$ obtained from step 1306 is multiplied in the spatial domain by the multiplication operator, M. The product of the calculation in step 1314 is transformed in step 1316 by a 2D FFT backwards into the spectral domain to yield the spectral contrast current density, represented by $(J_x^c, J_y^c, J_z^c)(m_1, m_2, z)$. In step 1318 the spectral contrast current density, is placed back in the 4D array.

In order to complete the calculation of the approximation of the known incident electrical field, $E^{inc}$ the Green's function's interaction with the background is calculated for each mode, $m_1$, $m_2$, by steps 1114 to 1122 in the same manner as described with reference to the corresponding identically numbered steps in FIG. 11. As described with reference to FIG. 11, steps 1116 to 1120 involve solving 1118 the regularized linear system of equations between first and second discrete transformation steps 1116 and 1120 to compute values of the regularized expansion coefficient vector, γ. Thus the dashed box 1350 including steps 1116 to 1120 corresponds to the steps described with reference to FIGS. 17A and 17B, which provide a more detailed description.

In step 1320 the result of the interaction of the spectral Green's function of the background, $\overline{G}$, and the spectral contrast current density, J, is placed back in the 4D array. Finally in step 1322 the calculation of the approximation of the known incident electrical field, $E^{inc}$ is completed with the subtraction of the result of step 1320 from the total electric field fed forward from step 1312 and the final step 1324 reorganises the 4D array in a vector. The means every four-dimensional index of the 4D array is uniquely related to a one-dimensional index of the vector.

US patent application publication no. US2013/0066597 A1, which is incorporated herein by reference, disclosed a contrast-source inversion (CSI) algorithm suitable for reconstructing the grating profile in a metrology application. An embodiment involves numerically solving a volume integral equation for a current density, J. It employs the implicit construction of a vector field, $F^S$, that is related to the electric field, $E^S$, and a current density, J, by a selection of continuous components of linear combinations of E and J, the vector field, F, being continuous at one or more material boundaries, so as to determine an approximate solution of a current density, J. The vector field, F, is represented by at least one finite Fourier series with respect to at least one direction, x, y, and the step of numerically solving the volume integral equation comprises determining a component of a current density, J, by convolution of the vector field, F, with a convolution operator, M. The convolution operator, M, comprises material and geometric properties of the structure in the x, y directions. The current density, J, may be represented by at least one finite Fourier series with respect to the x, y directions. Further, the continuous components can be extracted using convolution operators, $P_T$ and P, acting on the electric field, E, and current density, J.

Figure 14:
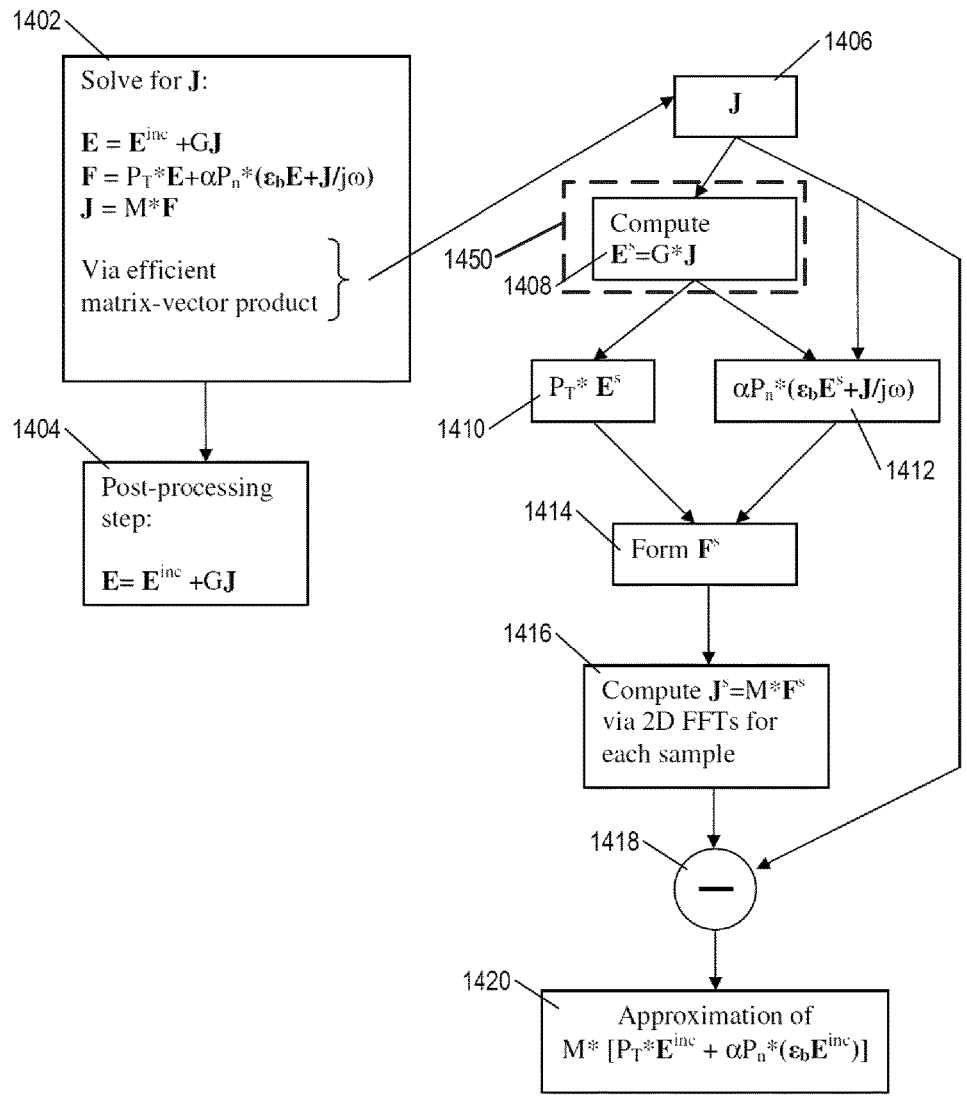
FIG. 14 depicts a method of solving the VIM formula with contrast source inversion, in accordance with an embodiment of the present invention.

FIG. 14 illustrates another embodiment of the present invention based on the disclosure of US2013/0066597 A1.

FIG. 14 shows the step 1402 of solving the VIM system for a current density, J, by employing an intermediate vector field, F, formed using continuous-component-extraction operators, with a post-processing step 1404 to obtain a total electric field, E, by letting the Green's function operator act on a current density, J. FIG. 14 also shows at the right hand side a schematic illustration of performing an efficient matrix-vector product 1406 to 1420 to solve the VIM system iteratively. This starts with a current density, J, in step 1406. The first time that J is set up, it can be started from zero. After that initial step, the estimates of J are guided by the iterative solver and the residual. In step 1408 the interactions and rank-1 projections between the Green's function, G, and the contrast current density, J, are computed to yield the scattered electric field, $E^s$. In accordance with an embodiment of the present invention, integration of a pseudo-spectral polynomial expansion is performed by solving a regularized linear system of equations. In the same way as discussed with reference to FIGS. 11 and 12, two regularized systems may be solved: one for the upward integration and one for the downward integration. Two uncoupled systems can be brought under one matrix equation that is twice as large. The linear system of equations may be regularized by modifying the linear system to compensate for expansion coefficients prone to conditioning-related errors by defining an extended regularized expansion coefficient vector. Regularizing the linear system of equations may include generating a function, F(k), at sample points in the orthogonal direction, the function comprising expansion coefficients prone to conditioning-related errors, such that the modifying of the linear system compensates for the function, F(k). The dashed box 1450 corresponds to the steps enclosed by dashed box 1550 described with reference to FIG. 15 and the steps described with reference to FIGS. 17A and 17B. Also, intermediate vector field, F, is computed in step 1414 using a convolution with two continuous-component-extraction operators $P_T$ and $P_n$ acting on the scattered electric field, $E^s$, and the current density, J. Thus the first continuous-component-extraction operator, $P_T$, is used to extract the continuous component of the electromagnetic field, $E^s$ in step 1410 and the second continuous-component-extraction operator, $P_n$, is used to extract the continuous component of the scaled electromagnetic flux density, $D^s$, in step 1412. In step 1416, the field-material interaction operator (M) operates on the extracted continuous components. Step 1414 represents forming a vector field, $F^s$, that is continuous at the material boundary from the continuous component of the electromagnetic field obtained in step 1410 and the continuous component of the scaled electromagnetic flux density obtained in step 1412. The step of determining components of the contrast current density 1416 is performed by using a field-material interaction operator M to operate on the vector field, $F^s$. Steps 1410 to 1416 are performed for each sample point in z with the convolutions being performed via FFTs. The convolution may be performed using a transformation such as one selected from a set comprising a fast Fourier transform (FFT) and number-theoretic transform (NTT). Operation 1418 subtracts the two computed results $J^s$ from J to obtain an approximation of $J^{inc}$ in 1420, related to the incident electric field $E^{inc}$. Because steps 1406 to 1420 produce update vectors then the post-processing step 1404 is used to produce the final value of the total electric field, E.

Rather than a separate post-processing step 1404 the sum of all the update vectors may be recorded at step 1408 in order to calculate the scattered electric field, $E^s$ and the post processing step becomes merely adding the incident electric field, $E^{inc}$ to the scattered electric field. However, that approach increases the storage requirements of the method, whereas the post-processing step 1404 is not costly in storage or processing time, compared to the iterative steps 1406 to 1420.

Figure 15:
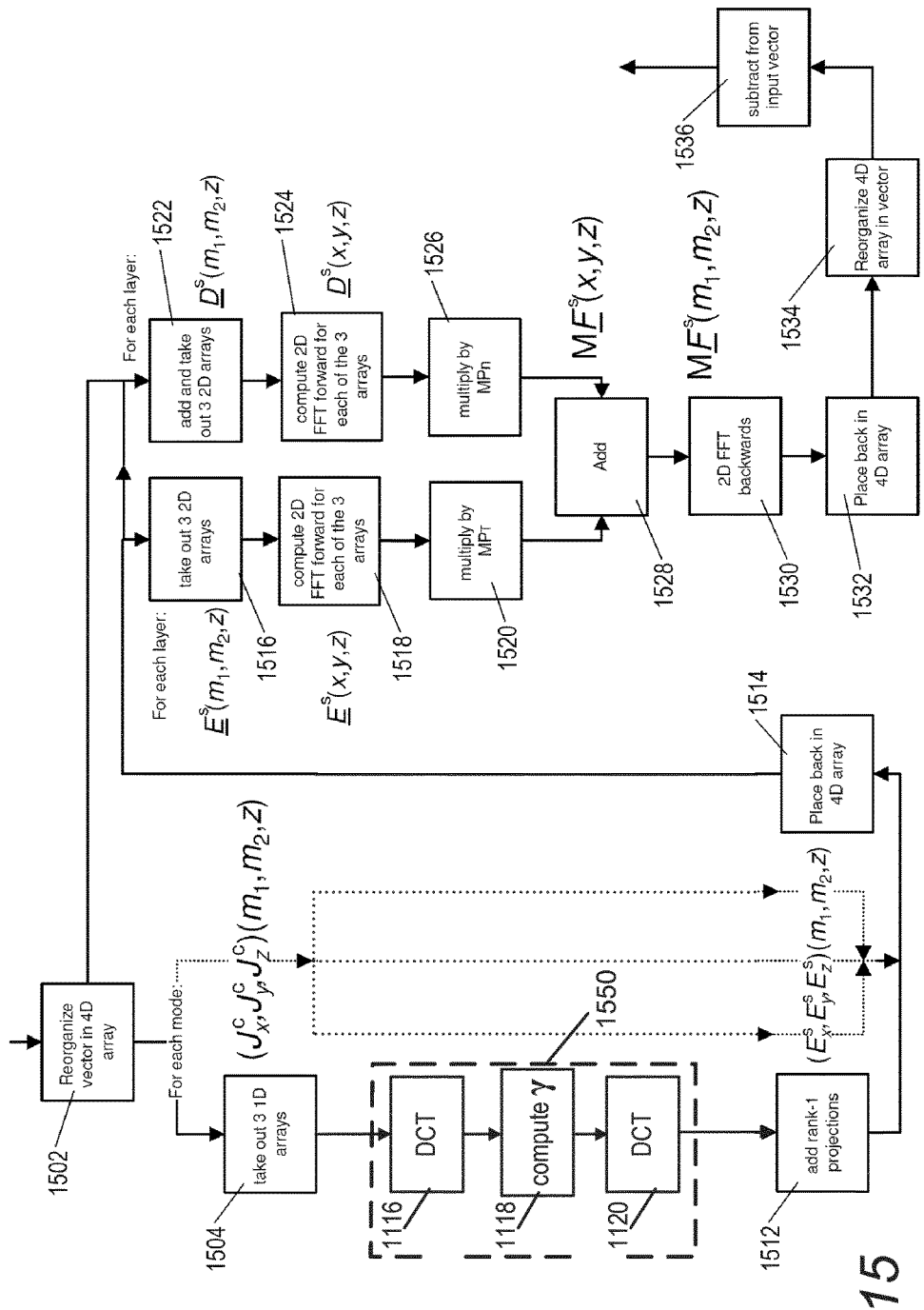
FIG. 15 is a flow chart of the computation of update vectors using the VIM formula with contrast source inversion, in accordance with an embodiment of the present invention.

FIG. 15 is a flow chart of the computation of update vectors in accordance with an embodiment of the present invention, based on the disclosure of US2013/0066597 A1. The flow chart of FIG. 15 corresponds to the right hand side (steps 1406 to 1420) of FIG. 14.

In step 1502 the vector is reorganized in a 4D array.

Subsequently, the Green's function's interaction with the background is calculated for each mode, $m_1$, $m_2$, by steps 1504 to 1514 in the same manner as described with reference to the corresponding steps numbered 1114 to 1124 in FIGS. 11 and 1114 to 1320 in FIG. 13. As described with reference to FIGS. 11 and 13, steps 1116 to 1120 involve solving 1118 the regularized linear system of equations between first and second discrete transformation steps 1116 and 1120 to compute values of the regularized expansion coefficient vector, γ. Thus the dashed box 1550 including steps 1116 to 1120 corresponds to the steps described with reference to FIGS. 17A and 17B, which provide a more detailed description.

Then for each sample point in z (that is, for each layer), steps 1516 to 1530 are performed. In step 1516 three 2D arrays are taken out of the 4D array. These three 2D arrays $(E_x, E_y, E_z)(m_1, m_2, z)$ correspond to the Cartesian components of the scattered electric field, E, each having the 2 dimensions corresponding to $m_1$ and $m_2$. The convolution of the continuous vector field, represented by $(F_x, F_y, F_z)(m_1, m_2, z)$ begins with the computation in step 1518 of the 2D FFT forward into the spatial domain for each of the three arrays, represented by $(E_x, E_y, E_z)(m_1, m_2, z)$. In step 1520 the Fourier transform $(E_x, E_y, E_z)(x, y, z)$ obtained from step 1518 is multiplied in the spatial domain by the spatial multiplication operator $MP_T(x, y, z)$, which has two functions: first it filters out the continuous components of the scattered electric field by applying the tangential projection operator $P_T$, thus yielding the tangential components of the continuous vector field, F, and second it performs the multiplication by the contrast function M, which relates the continuous vector field F to the contrast current density J, regarding only the scattered fields.

The scattered electric field, $(E_x, E_y, E_z)$ $(m_2, m_2, z)$, placed in the 4D array at step 1514 is fed into both step 1516, as discussed above, and step 1522, as discussed below.

In step 1522, for each sample point in z (that is, for each layer) a scaled version of the scattered electric flux density, D, is formed as the scaled sum of the scattered electric field, obtained from step 1514, and the contrast current density, fed forward from step 1502, after which three 2D arrays are taken out, corresponding to the Cartesian components of D in the spectral domain. In step 1524 the 2D FFT of these arrays are performed, yielding the Cartesian components $(D_x, D_y, D_z)(x, y, z)$ in the spatial domain. In step 1526 these arrays are multiplied in the spatial domain by the multiplication operator, $MP_n$, which has two functions: first the normal component of the scaled flux density, which is continuous, is filtered out and yields the normal component of the continuous vector field, F̲, and second it performs the multiplication by the contrast function M, which relates the continuous vector field F to the contrast current density J, regarding only the scattered fields. Then in step 1528 the results of the steps 1520 and 1526 are combined to yield the approximation of the operation MF, for all components of the continuous vector field, F, i.e. both the tangential and the normal components. Then MF is transformed in step 1530 by a 2D FFT backwards into the spectral domain to yield the approximation of the spectral contrast current density, represented by M̲F̲$(m_1, m_2, z)$. In step 1532 the resulting spectral contrast current density related to the scattered field, is placed back in the 4D array and subsequently transformed back to a vector in step 1534. This means every four-dimensional index of the 4D array is uniquely related to a one-dimensional index of the vector. Finally in step 1530 the calculation of the approximation of the known contrast current density related to the incident electric field, $J^{inc}$, is completed with the subtraction of the result of step 1534 from the total contrast current density fed forward from the input of step 1502.

Chebyshev Interpolation Algorithm

In an embodiment, the discretization of the sequence of one-dimensional integral equations, along the longitudinal, aperiodic (z) direction, in a volume integral method of calculating electromagnetic scattering properties is addressed. Originally, these integral equations have been discretized with local piecewise-linear basis functions for expanding the contrast-current density and point matching for testing. The merit of this approach is that it leads to a simple and low-complexity algorithm of O(N) when the semi-separability of the 1D Green's function is exploited or of O(N log N) when the convolution property is exploited, where N is the number of basis functions and sample points. Further, the geometry of a grating in the z-direction can be built from slices and the discretization can be handled per slice.

However, a disadvantage is that the convergence of the interpolation error along the z direction is limited to second order, due to the piecewise-linear expansion functions. This is in contrast with RCWA, where the behavior for each mode is known analytically in terms of exponential functions with propagation coefficients that follow from the eigenvalue decomposition. Since we do not want to introduce expensive eigenvalue computations in the volume integral equation method, we are looking for an alternative that leads to fast convergence of the interpolation error, while maintaining a low-complexity matrix-vector product for the sequence of one-dimensional integral equations.

A natural way of obtaining higher-order convergence for the interpolation is to use a polynomial basis of higher order. There are however two aspects that should be kept in mind in reasoning along these lines. First of all, to obtain higher-order convergence, the function to be interpolated should be sufficiently regular to allow for a high-order interpolation, i.e. the function should be continuously differentiable to sufficiently high degree on the entire interval of interpolation. In a volume integral method, this means that high-order interpolation can only be applied per slice, since the spectral components of the contrast current density, which are the interpolated functions in the integral equations, can exhibit several kinds of discontinuities across a slice boundary.

The second aspect is that the interpolation and integration with the integration kernel, i.e. the spectral Green's functions, should yield a low-complexity algorithm for the corresponding matrix-vector product. For low-order piecewise-linear expansions, this was simple since the limited support of each basis function yields low-order recurrence relations, i.e. one can integrate from one sample point to the next via a few multiplications and additions of already computed function values and integrated function values. For higher-order polynomials, this is typically not the case since the interpolation points spread along the entire integration interval. Therefore, another mechanism is needed to yield a low-complexity matrix-vector product. The mechanism used here is that a short recurrence relation, involving only a few (and fixed number of) previously computed coefficients and weights, can be derived between the expansion coefficients of orthogonal polynomials before and after integration with the one-dimensional Green's function kernels and that the weighted sum of polynomials can be evaluated at well-chosen specific points via a low-complexity algorithm. In particular, we choose a basis of Chebyshev polynomials of the first kind, which can be evaluated at so-called Chebyshev nodes by a discrete cosine transformation (DCT), which is directly related to a Fast Fourier Transform (FFT).

Green's Functions and Integral Equations

In a volume integral method, it is required to integrate a spectral component of the contrast current density, denoted $j_m(z)$, with one-dimensional Green's function kernels as well as its first and second derivative with respect to z, i.e.

$$\partial_z^n \int_a^b j_{i,m}(z') \exp(-\gamma_m |z - z'|) dz', \qquad (1)$$

where $i \in \{x,y,z\}$ denotes the Cartesian component of the contrast current density, $n \in \{0,1,2\}$ denotes the order of differentiation with respect to z, and (after differentiation) z takes on predefined discrete values, which are independent of m. These integrals can be rewritten as linear combinations of the integrals $$G_1(z) = \int_a^z j_{i,m}(z') \exp(-\gamma_m |z - z'|) dz', \qquad (2)$$

$$G_2(z) = \int_z^b j_{i,m}(z') \exp(-\gamma_m |z - z'|) dz', \qquad (3)$$

where $z \in [a,b]$. The class of kernels to which these integral-equation kernels belong are the so-called semi-separable kernels. These integrals also bear a strong resemblance to Volterra integral equations. Owing to the splitting of the integrations in an upward and a downward integration, the absolute values in the exponential function can be removed, which yields the expressions $$G_1(z) = \int_z^a j_{i,m}(z') \exp[-\gamma_m(z - z')] dz', \qquad (4)$$

$$G_2(z) = \int_z^b j_{i,m}(z') \exp[\gamma_m(z - z')] dz'. \qquad (5)$$

Although it is now possible to bring $\exp(\pm \gamma_m z)$ outside the integral, one needs to be careful in implementing this in a numerical sense, since $\gamma_m$ can be large and positive whereas z takes on values in [a,b], which may result in very large or very small numbers for the exponential.

Preliminaries on Chebyshev Polynomials of the First Kind

Chebyshev polynomials of the first kind have been used quite a lot for interpolation of functions, thereby forming a subclass of so-called pseudo-spectral methods. Pseudo-spectral methods are known for their high order of convergence with respect to interpolation errors on very smooth functions. Further, Chebyshev polynomials form a set of orthogonal polynomials with the peculiar property that they exhibit orthogonality both in the form of continuous functions and in the form of discrete (sampled) functions. They owe these properties to their intimate relation to Fourier expansions, for which also the continuous and discrete orthogonality relations hold, as exploited in continuous and discrete Fourier transforms.

The Chebyshev polynomial of the first kind $T_n(x)$ of order $n=0, 1, 2, \ldots$ is defined on the interval $x \in [-1,1]$ as $$T_n(x) = \cos(n \arccos(x)). \qquad (6)$$

Although the definition can be extended beyond the interval $[-1,1]$, we will not need an extended definition. For the derivative with respect to x, we easily derive the following relations $$\frac{d}{dx} T_0(x) = 0, \qquad (7)$$

$$\frac{d}{dx} T_1(x) = T_0(x), \qquad (8)$$

$$\frac{1}{2} \frac{d}{dx} T_2(x) = 2 T_1(x), \qquad (9)$$

$$\frac{1}{n+1} \frac{d}{dx} T_{n+1}(x) - \frac{1}{n-1} \frac{d}{dx} T_{n-1}(x) = 2 T_n(x), \text{ for } n \geq 2. \qquad (10)$$

The definition of the Chebyshev polynomials of the first kind also allows for a direct derivation of the orthogonality relation in the continuous case, by substitution of $x = \cos(t)$, i.e.

$$(T_m, T_n) = \int_{-1}^{1} \frac{T_m(x) T_n(x)}{\sqrt{1-x^2}} dx = \begin{cases} 0 & \text{if } m \neq n \\ \pi & \text{if } m = n = 0 \\ \frac{\pi}{2} & \text{if } m = n \neq 0 \end{cases}. \qquad (11)$$

With this orthogonality relation, expansions of functions in terms of Chebyshev polynomials of the first kind can be established on the interval $x \in [-1,1]$, i.e.

$$f(x) = \sum_{n=0}^{\infty} \hat{f}_n T_n(x), \qquad (12)$$

where the expansion coefficients are obtained as $$(f, T_m) = \int_{-1}^{1} \frac{f(x) T_m(x)}{\sqrt{1-x^2}} dx =$$

$$\int_{-1}^{1} \frac{\sum_{n=0}^{\infty} \hat{f}_n T_n(x) T_m(x)}{\sqrt{1-x^2}} dx = \sum_{n=0}^{\infty} \hat{f}_n \int_{-1}^{1} \frac{T_n(x) T_m(x)}{\sqrt{1-x^2}} dx = \frac{\pi \varepsilon_m}{2} \hat{f}_m \qquad (13)$$

where it has been assumed that the order of integration and summation can be interchanged, e.g. owing to uniform convergence and where $$\varepsilon_m = \begin{cases} 2 & n = 0 \\ 1 & n > 0 \end{cases}, \qquad (14)$$

is the Neumann symbol. The presence of the Neumann symbol has inspired several authors to introduce the $\Sigma'$ notation, i.e.

$$\sum_{n=0}^{\infty} {}' c_n T_n(x) = \frac{1}{2} c_0 T_0(x) + \sum_{n=1}^{\infty} c_n T_n(x). \qquad (15)$$

For later convenience, the expansion of the exponential function in terms of Chebyshev polynomials of the first kind on the interval $[-1,1]$ is given as $$\exp(qx) = 2\sum_{n=0}^{\infty}{}' I_n(q)T_n(x) = I_0(q)T_0(x) + 2\sum_{n=1}^{\infty} I_n(q)T_n(x), \quad (16)$$

where $I_n(q)$ is the modified Bessel function of the first kind of order n and argument q. This expansion follows from the generating function for Bessel functions of the first kind and the relation between the Chebyshev polynomials and the cosine [5].

Beside the above continuous orthogonality properties between the polynomials, there is also a discrete orthogonality property between the polynomials. The Chebyshev polynomials are then sampled at so-called Chebyshev nodes, which can be defined in two different ways: the closed rules and the open rules. The closed Chebyshev nodes are defined as the N+1 zeros of the polynomial $(1-x^2)T'_N(x)$, where the prime indicates the derivative with respect to x, i.e.

$$x_k = \cos\left(\frac{\pi k}{N}\right), \quad k = 0, \ldots, N, \quad (17)$$

In this case, the Chebyshev nodes include the boundary of the domain of definition, i.e. ±1. These Chebyshev nodes can be employed as abscissae, or sample points, in Chebyshev Gauss-Lobatto quadrature rules. In view of the inclusion of the endpoints of the domain, these rules are known as "closed quadrature rules", see [1] and [4, p. 106-112]. These nodes give rise to the discrete orthogonality relation $$\langle T_m, T_n \rangle = \sum_{k=0}^{N} \frac{1}{d_k} T_m(x_k)T_n(x_k) = \begin{cases} 0 & \text{if } m \neq n \\ Nd_n & \text{if } 0 \leq m = n \leq N \end{cases}, \quad (18)$$

for m,n≤N, where $$d_k = \begin{cases} 2 & \text{if } k = 0 \vee k = N \\ 1 & \text{if } 1 \leq k \leq N-1 \end{cases}. \quad (19)$$

Since we will be applying Chebyshev expansions per slice and since we already have a mechanism to couple responses from individual slices via field values sampled at the top and bottom of each slice, our interest lies with the applications of the closed rules, i.e. the Chebyshev nodes that include the endpoints of the interval [−1,1], and we will assume that the nodes corresponding to the closed rules are used. At the end of this section, a brief overview is given for the case of the so-called "open rules".

The discrete orthogonality relations can be used to construct order N function interpolations of $f(x)$, based on the samples $f(x_k)$ at the Chebyshev nodes, i.e.

$$f(x) \approx \sum_{n=0}^{N} \hat{f}_n T_n(x), \quad (20)$$

where $$f(x_k) = \sum_{n=0}^{N} \hat{f}_n T_n(x_k), \quad (21)$$

owing to the interpolation property at the Chebyshev nodes. Exploitation of the orthogonality relation for the closed rules above yields $$\langle f, T_m \rangle = \sum_{k=0}^{N} \frac{1}{d_k} f(x_k) T_m(x_k) = \sum_{k=0}^{N} \frac{1}{d_k} \left[ \sum_{n=0}^{N} \hat{f}_n T_n(x_k) T_m(x_k) \right]$$

$$= \sum_{n=0}^{N} \hat{f}_n \left[ \sum_{k=0}^{N} \frac{1}{d_k} T_n(x_k) T_m(x_k) \right] = N d_m \hat{f}_m. \quad (22)$$

Hence the expansion coefficients $\hat{f}_n$ can be determined as $$\hat{f}_n = \quad (23)$$

$$\frac{1}{Nd_n} \langle f, T_n \rangle = \frac{1}{Nd_n} \sum_{k=0}^{N} \frac{1}{d_k} f(x_k) T_n(x_k) = \frac{1}{Nd_n} \sum_{k=0}^{N} \frac{1}{d_k} f(x_k) \cos\left(\frac{\pi k n}{N}\right).$$

The latter formula can be interpreted as a discrete cosine transformation of type I (DCT-I). This interpretation is very important since the DCT yields all the expansion coefficients $\hat{f}_n$ for n=0, ..., N in one application of the DCT acting on the vector of length N+1 that contains the sampled function values $f(x_k)$ for k=0, ..., N. Moreover, the DCT is a low-complexity algorithm of O(N log N) for well-chosen values of N, owing to its relation to the Fast Fourier Transform (FFT). In fact, The DCT-I of length N+1 is exactly equivalent (up to an overall scale factor of 2), to an FFT of 2N real numbers with even symmetry. Consequently, 2N must have a factorization in small prime numbers in order to yield an efficient algorithm. The DCT-I has e.g. been implemented in the software package FFTW. It is worth noting that the DCT of type I is a scaled version of its own inverse. This means that the sample-point values $f(x_k)$ can be regenerated from the expansion coefficients $\hat{f}_n$ via a DCT-I.

The presence of the multiplication factor $1/d_n$ in summations with Chebyshev polynomials is in some literature denoted by a double prime, i.e.

$$\sum_{n=0}^{N} {}'' \hat{f}_n T_n(x) = \sum_{n=0}^{N} \frac{1}{d_n} \hat{f}_n T_n(x). \quad (24)$$

Some remarks are given below with respect to the open Chebyshev nodes. One can define the open Chebyshev nodes as the N+1 zeros of $T_{N+1}$, which do not include the endpoints of the domain, as $$x_k = \cos\left(\frac{\pi(2k+1)}{2(N+1)}\right), \quad k = 0, \ldots, N, \quad (25)$$

which gives rise to the orthogonality relation $$\langle T_m, T_n \rangle = \sum_{k=0}^{N} T_m(x_k) T_n(x_k) = \begin{cases} 0 & \text{if } m \neq n \\ N+1 & \text{if } m = n = 0 \\ (N+1)/2 & \text{if } 1 \leq m = n \leq N \end{cases}, \quad (26)$$

for m,n<N. These Chebyshev nodes can also be employed as abscissae in Chebyshev Gauss-Lobatto quadrature rules. In view of the exclusion of the endpoints of the domain, these rules are known as "open rules", see [1]. These quadrature rules are obtained by integrating the overall interpolation polynomial, expressed in terms of Chebyshev polynomials of the first kind, and the abscissae are then given by the open nodes. The corresponding multiplication factors for the Chebyshev polynomials are again obtained via a DCT, but now of type II (DCT-II) and the inverse operation of the DCT-II is the DCT of type III (DCT-III). Both DCT-II and DCT-III have also been implemented in FFTW and have a computational complexity of O(N log N).

For the case of a homogeneous slab illuminated by an obliquely incident plane wave with parallel or perpendicular polarization, two well-known 1D problems, we can follow the article by Kang, Koltracht, and Rawitscher [2]. The authors exploit Chebyshev expansions for a class of 1D kernels that include the so-called semi-separable kernels, which are kernels k(z,z') of the form $$k(z, z') = \begin{cases} k_1(z)k_2(z') & \text{if } a \le z \le z' \\ k_3(z)k_4(z') & \text{if } z' \le z \le b \end{cases}, \quad (27)$$

defined on the interval [a,b]. In essence, the approach followed by the authors is to extend the domain of the kernels $k_1$ to $k_4$ to the entire interval [a,b] in a smooth manner and subsequently employ Chebyshev expansions for these kernels. Since the semi-separability of the kernel leads to a significant computational advantage in the discretized case, it seemed best to maintain the semi-separability while expanding the kernels. For the case of the Green's function of a 1D slab, which is proportional to exp(−γ|z−z'|), the kernels $k_1(z)$ to $k_4(z)$ become functions exp(±γz) on the interval [0,d], i.e. the position of the slab. Clearly, when γ has a real part, two of these kernels demonstrate exponential growth and the other two demonstrate exponential decay, which can be detrimental for numerical stability and accuracy of the overall algorithm.

Initial tests, following the implementation of the proposed algorithm in [2], demonstrated that high-accuracy answers could be obtained for the slab, compared to the exact solution, in case of propagating waves where γ is a purely imaginary number. The tests showed exponential convergence with respect to the order of the Chebyshev expansion. For example, for a slab with a thickness of half a wavelength, only 17 Chebyshev polynomials were needed to obtain an answer up to machine precision. This has to be compared with the $O(N^{-2})$ convergence rate of piecewise-linear expansions, which are used in known systems using volume integral methods.

Figure 16:
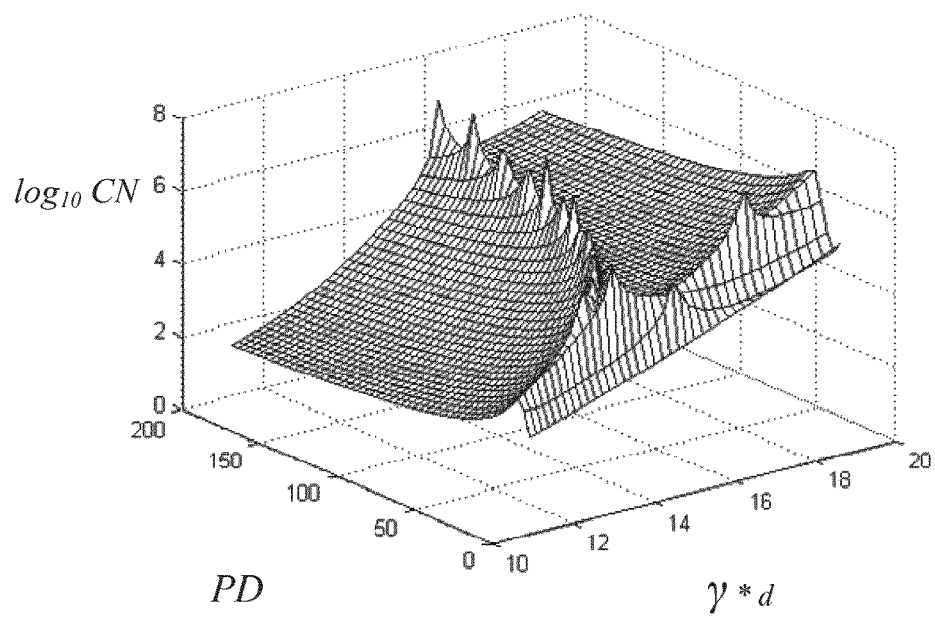
FIG. 16 illustrates the condition number of a linear system corresponding to a discretized version of the VIM formula for a 1-dimensional dielectric slab on a logarithmic scale versus real part of propagation coefficient times the thickness and versus the polynomial degree PD of the expansion.

FIG. 16 illustrates condition number CN on a logarithmic scale versus real part of propagation coefficient γ times the thickness and versus the polynomial degree PD of the expansion, for the approach proposed in [2]. The thickness of the slab was d=0.5λ and γ is purely real. The polynomial degree indicates the number of Chebyshev polynomials taken into account.

An investigation was made to see what happens to the accuracy and stability of the algorithm when evanescent waves are considered, i.e. when Re{γ}>0. It was observed that the convergence rate remains exponential but the condition number of the associated linear system increases rapidly when the real part of γ increases or when γ has a non-zero real part and the thickness of the slab increases, as shown in FIG. 16. When the number of evanescent modes that is taken into account in simulations using a volume integral method is increased, the iterative solver needs many iterations to converge, even for relatively low contrasts. When the number of modes is increased even further, the iterative solver fails to converge. These outcomes clearly indicate the ill-conditioning due to the proposed algorithm, since such iterative convergence issues never occurred before for identical low-contrast cases when a piecewise-linear expansion was used. Furthermore, there are theoretical results that demonstrate that general interpolation methods, including piecewise-linear expansions and expansions by Chebyshev polynomials, yield integral equations with a conditioning that approaches the conditioning of the continuous formulation, which is typically well-conditioned for integral equations of the kind discussed here. Hence the interpolation itself cannot be causing the ill conditioning. Consequently, the expansions of the kernels must somehow be responsible, which is in agreement with the concern that rapidly increasing and decaying exponentials form the kernels.

Analytic Integration Algorithm

The most appealing property of the approach proposed in [2] is that the matrix-vector product with respect to the Green's function has low computational cost, owing to the application of the DCT and the sparsity of the subsequent matrix-vector operations, in the form of the so-called left and right spectral integration matrices [2]. At first sight, it is not clear that such properties can be retained by resorting to another approach of integrating the product of Chebyshev polynomials and the Green's function, since the structure of the matrix-vector product depends on the kernel extension proposed in [2]. However, to gain insight in the origin of the instability noted in the preceding section, we will continue by deriving an exact integration procedure and at the same time we will demonstrate that the resulting algorithm is still of low complexity.

In analogy with Eq. (1), we expand the unknown current density in terms of a general polynomial $P_M(z)$ of degree M and consider the indefinite integral $$\int P_M(z) \exp(\gamma z) dz = Q_M(z) \exp(\gamma z), \quad (28)$$

where $Q_m(z)$ is again a polynomial of degree m. The formula is obtained by repeated partial integration. From a computational point of view, the key point is to relate the coefficients of $Q_m(z)$ to the coefficients of $P_m(z)$ and to have a rapid evaluation of the polynomials $P_m(z)$ and $Q_m(z)$ on a range of values of z. The rapid evaluation of the polynomials $P_m$ and $Q_m$ can be obtained by writing the polynomials as a sum of Chebyshev polynomials and simultaneously restricting the values of z to those of the abscissae of the underlying quadrature rule in the form of a DCT as indicated above in relation to the preliminary discussion of Chebyshev polynomials. To be able to apply the properties of the Chebyshev polynomials, it is important to first scale the interval of interest, i.e. z∈[a,b] to the interval t∈[−1,1] by introducing the scaling $$t = \frac{2(z-a)}{(b-a)} - 1, \quad (29)$$

$$q = \gamma \frac{b-a}{2}. \quad (30)$$

We continue by expanding the scaled polynomials $P_m$ and $Q_m$ in terms of Chebyshev polynomials and we rewrite Eq. (28) as $$\frac{b-a}{2}\exp\left(\frac{b+a}{b-a}q\right)\int \exp(qt)\sum_{m=0}^{M}{}'\alpha_m T_m(t)dt = \tag{31}$$

$$\frac{b-a}{2}\exp\left(\frac{b+a}{b-a}q\right)\exp(qt)\sum_{m=0}^{M}{}'\beta_m T_m(t),$$

where we would like to find all $\beta_m$ as a function of q and $\alpha_n$, $n \in \{0, \ldots, M\}$. The requested relation can be found by differentiating the above equation with respect to t, i.e.

$$\exp(qt)\sum_{m=0}^{M}{}'\alpha_m T_m(t) = \exp(qt)\left[q\sum_{m=0}^{M}{}'\beta_m T_m(t) + \sum_{m=0}^{M}{}'\beta_m \frac{dT_m(t)}{dt}\right]. \tag{32}$$

Hence we have the polynomial equation $$\sum_{m=0}^{M}{}'\alpha_m T_m(t) = q\sum_{m=0}^{M}{}'\beta_m T_m(t) + \sum_{m=0}^{M}{}'\beta_m \frac{dT_m(t)}{dt}. \tag{33}$$

By applying the relations (2) and subsequently integrating with respect to t, we arrive at $$\frac{1}{2}\alpha_0 T_1(t) + \frac{1}{4}\alpha_1 T_2(t) + \sum_{m=2}^{M}\alpha_m\left[\frac{T_{m+1}(t)}{2(m+1)} - \frac{T_{m-1}(t)}{2(m-1)}\right] = \tag{34}$$

$$q\left\{\frac{1}{2}\beta_0 T_1(t) + \frac{1}{4}\beta_1 T_2(t) + \sum_{m=2}^{m}\beta_m\left[\frac{T_{m+1}(t)}{2(m+1)} - \frac{T_{m-1}(t)}{2(m-1)}\right]\right\} +$$

$$\sum_{m=0}^{M}\beta_m T_m(t) + C,$$

where C denotes the integration constant due to indefinite integration. Note that the coefficients for $T_0(t)$ cannot be determined due to the integration constant C and therefore $T_0(t)$ has been removed from the above equation. By grouping the coefficients with equal Chebyshev polynomial, we arrive at the set of linear equations $$\frac{1}{2}\alpha_0 - \frac{1}{2}\alpha_2 = \frac{q}{2}(\beta_0 - \beta_2) + \beta_1, \tag{35}$$

$$\frac{1}{4}(\alpha_1 - \alpha_3) = \frac{q}{4}(\beta_1 - \beta_3) + \beta_2, \tag{36}$$

$$\frac{1}{2(m+1)}(\alpha_m - \alpha_{m+2}) = \frac{q}{2(m+1)}(\beta_m - \beta_{m+2}) + \beta_{m+1}, \tag{37}$$

$$m = 2, 3, \ldots, M-2$$

$$\frac{1}{2M}\alpha_{M-1} = \frac{q}{2M}\beta_{M-1} + \beta_M, \tag{38}$$

$$\frac{1}{2(M+1)}\alpha_M = \frac{q}{2(M+1)}\beta_M. \tag{39}$$

These linear relations can be summarized in terms of a matrix equation as $$U_M \beta_M = \frac{1}{q} D_M \alpha_M \tag{40}$$

where $$U_M = \begin{pmatrix} 1 & \frac{2}{q} & -1 & 0 & \cdots & & \cdots & 0 \\ 0 & 1 & \frac{4}{q} & -1 & 0 & & & \vdots \\ 0 & 0 & 1 & \frac{6}{q} & -1 & 0 & & \vdots \\ \vdots & \ddots & \ddots & \ddots & \ddots & \ddots & \ddots & \vdots \\ \vdots & & 0 & 1 & \frac{2(M-2)}{q} & -1 & 0 \\ \vdots & & & 0 & 1 & \frac{2(M-1)}{q} & -1 \\ \vdots & & & & 0 & 1 & \frac{2M}{q} \\ 0 & \cdots & \cdots & \cdots & & 0 & 0 & 1 \end{pmatrix}, \tag{41}$$

$$D_M = \begin{pmatrix} 1 & 0 & -1 & 0 & 0 & 0 & \cdots & 0 \\ 0 & 1 & 0 & -1 & 0 & 0 & \cdots & 0 \\ 0 & 0 & 1 & 0 & -1 & 0 & \cdots & 0 \\ \vdots & \ddots & \ddots & \ddots & \ddots & \ddots & & \vdots \\ \vdots & & & 0 & 1 & 0 & -1 & 0 \\ \vdots & & & & 0 & 1 & 0 & -1 \\ \vdots & & & & & 0 & 1 & 0 \\ 0 & \cdots & \cdots & \cdots & \cdots & 0 & 0 & 1 \end{pmatrix}, \tag{42}$$

and $$\alpha_M = \begin{pmatrix} \alpha_0 \\ \alpha_1 \\ \alpha_2 \\ \vdots \\ \vdots \\ \alpha_{M-2} \\ \alpha_{M-1} \\ \alpha_M \end{pmatrix}, \beta_M = \begin{pmatrix} \beta_0 \\ \beta_1 \\ \beta_3 \\ \vdots \\ \vdots \\ \beta_{M-2} \\ \beta_{M-1} \\ \beta_M \end{pmatrix}. \tag{43}$$

The matrix equation above yields a proper relation between the coefficients of the vectors $\alpha_M$ and $\beta_M$, in the sense that both matrices $U_M$ and $D_M$ are highly sparse and therefore the related complexity of solving the set of linear equations would, at least in principle, be of low complexity, i.e. O(N). At first sight, solving the linear system is very simply done by performing a back-substitution since $U_M$ is an upper-triangular matrix. Unfortunately, the matrix $U_M$ is extremely ill conditioned and consequently the resulting coefficients in the vector $\beta_M$ are extremely unreliable due to round-off. Further investigation has shown that the ill-conditioning of $U_M$ is due to a single singular value, which can become arbitrarily small. The ill-conditioning is perhaps best illustrated with a simple analytical example:

$$\int T_8(x)\exp(2x)dx = \tag{44}$$

$$\exp(2x) \times \left[\frac{1}{2}T_8(x) - 4T_7(x) + 28T_6(x) - 172T_5(x) + 888T_4(x) - 3724T_3(x) + 12060T_2(x) - 27844T_1(x) + 19952T_0(x)\right].$$

This example clearly demonstrates the extreme increase of the magnitude of the coefficients for decreasing polynomial order. Hence if the analytical result demonstrates this type of blow-up, the matrix $U_M$ must be inherently ill-conditioned, because the growth of the coefficients is bounded by the norm of the inverse of $U_M$. On the other hand, if the ill-conditioning is only related to a single singular vector, as was observed in several numerical tests, then it should be possible to split the linear system (40) into a well-conditioned system and a small ill-conditioned system. By itself, the ill-conditioned part of the system can still gives rise to numerical instabilities, but if it can be shown that this component of the total solution does not significantly contribute to the final solution for the overall integral equation, then there is still hope for a stable, well-conditioned, and efficient numerical algorithm for the integral equation.

To demonstrate the origin of the ill-conditioning, we separate the first column and the last row of the system in Eq. (40) and we rewrite the system as $$\beta_0 e_1 + B_R \beta_R = \frac{1}{q} D_R \alpha_M, \tag{45}$$

$$\beta_M = \frac{1}{q} \alpha_M,$$

where $B_R$ is obtained from $U_M$ by removing the first column and last row, $D_R$ is obtained from $D_M$ by removing the last row, and $\beta_R$ is obtained from $\beta_M$ by removing the first row, i.e. $\beta_0$ is taken out. Numerical tests show that $B_R$ is a well-conditioned matrix and therefore we can assume that $B_R^{-1}$ can be computed in a stable manner. Note that $B_R$ is a tri-diagonal matrix and therefore computing the LU decomposition of $B_R$ is an O(N) operation and subsequent forward and backward substitutions on the LU matrices are also O(N), owing to the fact that these matrices are bi-diagonal. Therefore computing a solution to an equation of the form $B_R x = y$ is O(N) in complexity.

The solution of the above system in terms of the inverse $B^{-1}$ is given by $$\beta_0 = \frac{1}{q} \frac{e_M \cdot [(B_R^{-1} D_R) \alpha_M] - \alpha_M}{e_M \cdot (B_R^{-1} e_1)}, \tag{46}$$

$$\beta_R = B_R^{-1} \left[ \frac{1}{q} D_R \alpha_M - \beta_0 e_1 \right], \tag{47}$$

where $e_k$ is the k-th unit vector, i.e. a vector with zeros everywhere except at the k-th entry. It is now readily seen, by using norm estimates and the observations that $B_R^{-1}$ and $D_R$ are linear operators with a small norm, that the amplitude $\beta_0$ above must be responsible for the instability in the numerical computations. In fact, it is the inner product $e_M \cdot (B_R^{-1} e_1)$ that is becoming extremely small when M>>1. The vector that corresponds with the large amplitude of $\beta_0$ is $B_R^{-1} e_1$ and the vector itself can be computed reliably, owing to the conditioning of $B_R$.

Let us now consider the structure of the solution of the overall expression for the integral under consideration on the interval $[-1, t]$ with $1 < t < 1$, i.e.

$$\int_{-1}^{t} \exp(-q(t-t')) \sum_{m=0}^{M} {}' \alpha_m T_m(t') dt' = \tag{48}$$

-continued $$\left\{ \exp[-q(t-t')] \sum_{m=0}^{M} {}' \beta_m T_m(t') \right\} \bigg|_{t'=-1}^{t'=t} =$$

$$\sum_{m=0}^{M} {}' \beta_m T_m(t) - \exp[-q(1+t)] \sum_{m=0}^{M} {}' \beta_m T_m(-1).$$

By writing the vector $\beta$ as the sum of the regularized part $\beta_R$ and a vector $v_R$ with amplitude controlled by $\beta_0$, as in Eq. (4), we obtain $$\int_{-1}^{t} \exp[-q(t-t')] \sum_{m=0}^{M} {}' \alpha_m T_m(t') dt' = \tag{49}$$

$$\sum_{m=1}^{M} \beta_{R,m} T_m(t) - \exp[-q(1+t)] \sum_{m=1}^{M} \beta_{R,m} T_m(-1) +$$

$$\beta_0 \underbrace{\left\{ \sum_{m=0}^{M} {}' v_{R,m} T_m(t) - \exp[-q(1+t)] \sum_{m=0}^{M} {}' v_{R,m} T_m(-1) \right\}}_{F(t)},$$

where we start counting the elements of $\beta_R$ from 1 instead of 0, and where $v_R$ is given by $$v_R = \begin{pmatrix} 1 \\ -B_R^{-1} e_1 \end{pmatrix}. \tag{50}$$

Hence, for a numerically stable expression for the integral above, the factor F(t) that is multiplied by $\beta_0$ must become very small to compensate for the growth in $\beta_0$, as a function of M. Maintaining the accuracy of this factor F(t) via numerical means is a complicated task, since severe cancellation can be expected between the two terms that together form this factor. As an extreme approach one could completely neglect the term F(t) by setting it to zero. Although numerical tests showed only a small impact when F(t) was neglected when testing for a homogeneous-slab configuration, the effect of this on the overall quality of the solution in a more complicated setting like a 3D spectral volume integral equation remains unclear. Therefore, we will now continue by applying a regularization technique proposed in the literature.

A Robust Algorithm for Analytic Integration

Obtaining a numerically stable solution for the linear system in Eq. (40) has been proposed in the literature via analytical regularization [5]. Below we follow the key steps of their exposition.

Instead of numerically constructing the function F(t) as in Eq. (49), an analytical approach is followed by recognizing that the first M−1 rows of $U_M$ in Eq. (40) with zero right-hand side (or the corresponding recurrence relations in Eq. (4) with $\alpha_m = 0$) are satisfied by the modified Bessel functions of the first kind, i.e.

$$I_{m-1}(-q) + \frac{2m}{q} I_m(-q) - I_{m+1}(-q) = 0, \tag{51}$$

$$m = 1, 2, 3, \ldots$$

where $I_m(-q)$ is the modified Bessel function of the first kind of order m and argument $-q$. The vector $I_M$ is now formed as $$I_M = \begin{pmatrix} I_0(-q) \\ I_1(-q) \\ I_2(-q) \\ \vdots \\ I_M(-q) \end{pmatrix} \qquad (52)$$

Consequently, if a vector $\beta_M$ is a solution of Eq. (40), then $\beta_M + \lambda I_M$ satisfies the first $M-1$ equations of the same linear system, i.e. only the last two equations are not satisfied. The key observation is now that the system of equations in Eq. (40) can be extended by adding one more row and column to $U_M$ and $D_M$, such that these then become $U_{M+1}$ and $D_{M+1}$ following the definitions of these matrices in Eqs (42), (41), and by extending the vectors $\alpha_M$ and $\beta_M$ with one row at the end that contains a zero. The extended vectors are denoted as $\alpha_{M+1}$ and $\beta_{M+1}$. Hence we have $$U_{M+1}\beta_{M+1} = \frac{1}{q}D_{M+1}\alpha_{M+1}, \qquad (53)$$

and $$U_{M+1}I_{M+1} = \begin{pmatrix} 0 \\ \vdots \\ 0 \\ I_M(-q) + \frac{2(M+1)}{q}I_{M+1}(-q) \\ I_{M+1}(-q) \end{pmatrix}, \qquad (54)$$

Subsequently, we define a vector $\gamma_{M+1}$ as $$\beta_{M+1} = \gamma_{M+1} + \lambda I_{M+1}, \qquad (55)$$

where we can now fix $\lambda$, owing to the fact that the last entry of $\beta_{M+1}$ is zero, i.e.

$$\lambda = -\frac{\gamma_{M+1}}{I_{M+1}(-q)}. \qquad (56)$$

We note that the exponential decay of the modified Bessel function, when $M > q$, shows that $\lambda$ can become quite large, so care will need to be taken for the numerical implementation. The definition of $\gamma_{M+1}$ introduces one extra degree of freedom in the set of equations, namely $\gamma_{M+}$, since the connection between $\lambda$ and $\gamma_{M+1}$ in Eq. (56) is in fact the last equation of the system Eq. (53).

By substituting the relations (55) and (56) in Eq. (53), we arrive at the linear system that holds for $\gamma_{M+1}$ $$\begin{pmatrix} 1 & \frac{2}{q} & -1 & 0 & \cdots & & \cdots & & 0 & 0 \\ 0 & 1 & \frac{4}{q} & -1 & 0 & & & & \vdots & \vdots \\ 0 & 0 & 1 & \frac{6}{q} & -1 & 0 & & & \vdots & \vdots \\ \vdots & & \ddots & \ddots & \ddots & \ddots & \ddots & & \vdots & \vdots \\ \vdots & & & 0 & 1 & \frac{2(M-2)}{q} & -1 & 0 & 0 \\ \vdots & & & & 0 & 1 & \frac{2(M-1)}{q} & -1 & 0 \\ \vdots & & & & & 0 & 1 & \frac{2M}{q} & -1 \\ 0 & \cdots & \cdots & \cdots & \cdots & 0 & 0 & 1 & \Delta \end{pmatrix} \begin{pmatrix} \gamma_0 \\ \gamma_1 \\ \gamma_2 \\ \gamma_3 \\ \vdots \\ \gamma_M \\ \gamma_{M+1} \end{pmatrix} = \qquad (57)$$

$$\frac{1}{q}D_M\alpha_M,$$

where the last equation of the original system has been removed, owing to Eq. (56), and $$\Delta = \frac{2(M+1)}{q} - \frac{I_{M+2}(-q)}{I_{M+1}(-q)}, \qquad (58)$$

which follows from the recurrence relation for the Bessel functions in Eq. (51). The linear system (57) is a set of $M+1$ equations for $M+2$ unknowns, i.e. $\gamma_0, \ldots, \gamma_{M+1}$. Consequently, there is freedom to fix one of the unknowns. Although a suggestion for this is given in [5], where a smaller matrix needs to be LU factorized at the expense of a more complicated book keeping, our choice is inspired by the preceding section and we will set $$\gamma_0 = 0, \qquad (59)$$

which essentially removes the first column of the matrix on the left-hand side. The resulting system for $\gamma_{M+1}$ is then $$\underbrace{\begin{pmatrix} \frac{2}{q} & -1 & 0 & \cdots & & \cdots & & 0 & 0 \\ 1 & \frac{4}{q} & -1 & 0 & & & & \vdots & \vdots \\ 0 & 1 & \frac{6}{q} & -1 & 0 & & & \vdots & \vdots \\ \vdots & \ddots & \ddots & \ddots & \ddots & \ddots & & \vdots & \vdots \\ \vdots & & 0 & 1 & \frac{2(M-2)}{q} & -1 & 0 & 0 \\ \vdots & & & 0 & 1 & \frac{2(M-1)}{q} & -1 & 0 \\ \vdots & & & & 0 & 1 & \frac{2M}{q} & -1 \\ 0 & \cdots & \cdots & \cdots & 0 & 0 & 1 & \Delta \end{pmatrix}}_{A(-q)} \begin{pmatrix} \gamma_1 \\ \gamma_2 \\ \gamma_3 \\ \vdots \\ \gamma_M \\ \gamma_{M+1} \end{pmatrix} = \qquad (60)$$

$$\frac{1}{q}D_M\alpha_M,$$

which closely resembles the regularized system in the preceding section. The matrix equation thus obtained has been found to be well-conditioned for a large range of real and complex values of q, except for q very close to zero. The latter case can be handled by multiplying the entire set of equations by q. Further, the solution of the linear system in Eq. (60) can be obtained efficiently owing to the tri-diagonal nature of the matrix A(−q), which yields bi-diagonal LU factors with efficient forward and backward substitution algorithms, as e.g. implemented in LAPACK (Linear Algebra PACKage).

Avoiding Cancellation in Subtracting Summations

We now go back to the original integral on the interval [−1,t] and consider the structure of the solution of the overall expression for the integral under consideration with 1<t<1 in terms of $\gamma_{M+1}$, i.e.

$$\int_{-1}^{t} \exp[-q(t-t')] \sum_{m=0}^{M} {}' \alpha_m T_m(t') dt' = \qquad (61)$$

$$\sum_{m=1}^{M} \gamma_m T_m(t) - \exp[-q(1+t)] \sum_{m=1}^{M} \gamma_m T_m(-1) -$$

$$\frac{\gamma_{M+1}}{I_{M+1}(-q)} \underbrace{\left\{ \sum_{m=0}^{M} {}' I_m(-q) T_m(t) - \exp[-q(1+t)] \sum_{m=0}^{M} {}' I_m(-q) T_m(-1) \right\}}_{F_A(-q,t)}.$$

Note that the first two summations in the above formula start at m=1, owing to the choice $\gamma_0=0$, as explained before. These equations closely resembles Eq. (49), but now the numerically computed vector $v_R$ has been replaced by the vector $I_M$, which has better known analytical properties that can be used to overcome the cancellation expected in the factor $F_A(-q,t)$. Loss of significant digits in this factor will rapidly translate in numerical instability due to the factor $1/I_{M+1}(-q)$, which exhibits exponential growth as a function of M once M>|q|.

To further investigate the factor $F_A(-q,t)$, we go back to Eq. (16). This representation for the exponential function in terms of Chebyshev polynomials can be used to derive an alternative expression for $F_A(t)$, see also [5], $$F_A(-q, t) = \sum_{m=0}^{M} {}' I_m(-q) T_m(t) - \exp[-q(1+t)] \sum_{m=0}^{M} {}' I_m(-q) T_m(-1) \qquad (62)$$

$$= \left( \frac{\exp(-qt)}{2} - \sum_{m=M+1}^{\infty} I_m(-q) T_m(t) \right) -$$

$$\exp[-q(1+t)] \left( \frac{\exp(q)}{2} - \sum_{m=M+1}^{\infty} I_m(-q) T_m(-1) \right)$$

$$= \exp[-q(1+t)] \sum_{m=M+1}^{\infty} I_m(-q) T_m(-1) -$$

$$\sum_{m=M+1}^{\infty} I_m(-q) T_m(t).$$

For the latter representation of $F_A(-q,t)$, we now include the factor $1/I_{M+1}(-q)$, i.e.

$$\frac{F_A(-q, t)}{I_{M+1}(-q)} = \qquad (63)$$

$$\exp[-q(1+t)] \sum_{m=M+1}^{\infty} \frac{I_m(-q)}{I_{M+1}(-q)} T_m(-1) - \sum_{m=M+1}^{\infty} \frac{I_m(-q)}{I_{M+1}(-q)} T_m(t).$$

Since the sequence $I_m(q)$ is typically an exponentially decaying sequence, we can expect that the series converge very fast and we note that the magnitude of the first term of the sequence is bounded by one. Consequently, the exponential increase of $1/I_{M+1}(-q)$ as a function of M has been successfully suppressed via this representation. As opposed to [5], we always use the latter representation for $F_A(-q,t)$, since we have experienced that it is always stable. A disadvantage is that this contribution has to be pre-computed whereas the former representation is easily included in the other summations.

The remaining task is now to actually compute the series of the above representation (63) for a given value of t, i.e.

$$S_{M+1}(-q, t) = \sum_{m=M+1}^{\infty} \frac{I_m(-q)}{I_{M+1}(-q)} T_m(t). \qquad (64)$$

An efficient way to do this, is to employ the Clenshaw's recurrence formula [3, p. 172-177]. Although both the Bessel functions and the Chebyshev polynomials can be chosen as the basis for the recurrence, we have employed the recurrence for the Chebyshev polynomials in Clenshaw's algorithm whereas the ratio of the Bessel functions have been generated in an earlier step based on the backward recurrence relation of Eq. (51), i.e. Miller's algorithm as $$R_m(z) = \frac{I_m(z)}{I_{m-1}(z)} = \frac{1}{\frac{2m}{z} + \frac{I_{m+1}(z)}{I_m(z)}} = \frac{1}{\frac{2m}{z} + R_{m+1}(z)} \qquad (65)$$

with a starting value of $R_N(z)=0$ for N at least 20 times larger than the maximum order of the modified Bessel functions that are taken into account in the summation. To arrive at the ratios needed for the summation, i.e. $I_m(-q)/I_{M+1}(-q)$ for m≥M+1, we note that these ratios can be obtained by multiplying the ratios $R_m(z)$ in a recursive manner, i.e.

$$\frac{I_{M+1}(-q)}{I_{M+1}(-q)} = 1, \qquad (66)$$

$$\frac{I_{M+2}(-q)}{I_{M+1}(-q)} = R_{M+2}(-q), \qquad (67)$$

$$\frac{I_{M+3}(-q)}{I_{M+1}(-q)} = \frac{I_{M+2}(-q)}{I_{M+1}(-q)} R_{M+3}(-q) = R_{M+2}(-q) R_{M+3}(-q), \qquad (68)$$

$$\frac{I_{M+n}(-q)}{I_{M+1}(-q)} = \frac{I_{M+n-1}(-q)}{I_{M+1}(-q)} R_{M+n}(-q) \; n = 3, 4, \ldots \qquad (69)$$

Sampling of the Integrals

The final step in the entire procedure is to introduce a mapping from the expansion coefficients of the current density to a new set of discrete variables. This is needed to be able to construct a finite linear system, i.e. a matrix-vector product for the integrals under consideration in (1). Basically, there are two approaches that can be followed. The first one is to approximate the entire integral as a sum of Chebyshev polynomials only, which means that two of the three terms in (61) need to be approximated in terms of Chebyshev polynomials, i.e. in essence $\exp[-q(1+t)]$ and $F_A(-q, t)$. The second approach is to sample the integral at prescribed points $t_k$, such that an efficient computation of the sums of Chebyshev polynomials can be achieved. Since we may wish to merge the Chebyshev expansion with a spatial sampling approach that is already functional in a volume integral method, it may be convenient to choose the second approach, i.e. to sample the integral.

The choice for the sampling points $t_k$ should follow from the application of the discrete cosine transform, since this is the most efficient way to evaluate a weighted sum of Chebyshev polynomials on a range of samples simultaneously. This leaves two possibilities: the open rules or the closed rules, as explained in Section 2. From the preceding discussions, it is easily seen that the end points $t=\pm 1$ are also present in the summations, which means that the closed rules are the most convenient choice. The closed rules coincide with DCT-I, as in Eq. (23), and the sample points are given by Eq. (17), i.e.

$$t_k = \cos\left(\frac{\pi k}{M}\right), \quad k = 0, \ldots, M. \tag{70}$$

The precise definition and implementation of the DCT-I in FFTW is given by $$DCT_I[f(t_k)](m) = f(t_0) + (-1)^m f(t_M) + 2\sum_{k=1}^{M-1} f(t_k)\cos\left(\frac{\pi km}{M}\right) = 2\sum_{k=0}^{M} \frac{1}{d_k} f(t_k) T_m(t_k), \tag{71}$$

where $DCT_I[f(t_k)](m)$ is the m-th element of the DCT-I of $f(t_k)$ and $d_k$ has been defined in Eq. (19) as $$d_k = \begin{cases} 2 & \text{if } k = 0 \vee k = M \\ 1 & \text{if } 1 \le k \le M-1 \end{cases}. \tag{72}$$

In the overall algorithm, there are now two steps that require a DCT-I. The first one is when the expansion coefficients $\alpha_m$ in Eq. (31) have to be determined from the sampled values of the contrast current density $j_i(z)$ at the Chebyshev nodes. By definition, we assume that we have the expansion $$j_i(z_k) = \sum_{m=0}^{M} {}' \alpha_m T_m(t_k) = \sum_{m=0}^{M} \frac{1}{d_m} \alpha_m^{(1)} T_m(t_k), \tag{73}$$

where $z_k=[(b+a)+(b-a)t_k]/2$ and $$\alpha_m^{(1)} = \begin{cases} \alpha_m & \text{if } m = 0, \ldots, M-1 \\ 2\alpha_m & \text{if } m = M \end{cases}. \tag{74}$$

From the relation in Eq. (22) we have $$\alpha_m^{(1)} = \frac{1}{M}\sum_{k=0}^{M} \frac{1}{d_k} j_i(z_k) T_m(t_k) = \frac{1}{2M} DCT_I[j(z_k)](m), \tag{75}$$

and hence $$\alpha_m = \begin{cases} \dfrac{1}{2M} DCT_I[j(z_k)](m) & \text{if } m = 0, \ldots, M-1 \\ \dfrac{1}{4M} DCT_I[j(z_k)](m) & \text{if } m = M \end{cases}, \tag{76}$$

which means that the coefficient $DCT_I[j(z_k)](M)$ must be multiplied by ½.

The second step that requires the DCT-I is when the coefficients $g_m$ of the Chebyshev expansion of the integrals $G_1(z)$ and $G_2(z)$ in Eq. (1) have been computed and the expansion needs to be evaluated at the Chebyshev nodes $z_k$, i.e.

$$G(z_k) = \sum_{m=0}^{M} {}' g_m T_m(t_k) = \sum_{m=0}^{M} \frac{1}{d_m} g_m^{(1)} T_m(t_k) = DCT_I[g_m^{(1)}](k), \tag{77}$$

where $$g_m^{(1)} = \begin{cases} g_m & \text{if } m = 0, \ldots, M-1 \\ 2g_m & \text{if } m = M \end{cases}. \tag{78}$$

Full Matrix-Vector Product

Let us now go back to the original integrals $G_1(z)$ and $G_2(z)$ defined in (1) and summarize the steps taken so far. The computation consists of a preparation phase, which needs to be performed once, and an execution phase, which can be performed many times as a matrix-vector product.

The preparation phase consists of the following steps:
1. Scale interval [a,b] to [−1,1] and scale $\gamma_m$ to q, as in Eq. (4).
2. Choose maximum order of Chebyshev expansion: M.
3. Initialize DCT-I of length M+1.
4. Compute the Chebyshev nodes for the closed rules as in Eq. (17): $t_k$.
5. Compute the elements of the tri-diagonal matrix A(−q) in Eq. (60).
6. Compute LU factorization of A(−q) using LAPACK.
7. Compute the function $F(k)=F_A(-q,t_k)/I_{M+1}(-q)$ in Eq. (63) using the Clenshaw algorithm as explained in Section 5.1.
8. Compute the functions $v^1(k)=\exp[-q(1+t_k)]$ and $v^2(k)=\exp[-q(1-t_k)]$.

It is noted here that for the integral $G_2$, the matrix $A(q)$ is needed, but we can exploit the LU decomposition of A(−q) for that because $A(q)=A(-q)^T$. Similarly, for $G_2$ we need $A(q,t_k)/I_{M+1}(q)=F_A(-q,-t_k)/I_{M+1}(-q)=F(M-k)$ and the role of $v^1(k)$ and $v^2(k)$ is interchanged, owing to the anti-symmetry in the nodes $t_k=-t_{M-k}$.

The execution phase consists of the following steps:
1. Compute the expansion coefficients $\alpha_m$ of the current density, as in Eq. (76), via a DCT-I.
2. Compute $D_M \alpha_M$ with $D_M$ defined in Eq. (42).
3. Compute the coefficients of the vector $\gamma_{M+1}^1$ and $\gamma_{M+1}^1$ as the solution of Eq. (60), i.e.

$$A(-q)\gamma^1 = D_M \alpha_M, \tag{79}$$

$$A(q)\gamma^2 = D_M \alpha_M, \tag{80}$$

using the precomputed LU factors of A(−q).
4. Define $\gamma^{1*}=(0,\gamma_1^1, \ldots, \gamma_{M-1}^1, 2\gamma_M^1)$ and $\gamma^{2*}=(0, \gamma_1^2, \ldots, \gamma_{M-1}^2, 2\gamma_M^2)$.
5. Compute $H_1(k)=DCT_I[\gamma_m^{1*}](k)$ and $H_2(k)=DCT_I[\gamma_m^{2*}](k)$ 6. Compute $$G_1(k) = \frac{1}{q}\{H_1(k) - H_1(0)v_k^1 - \gamma_{M+1}^1 F(k)\}.$$

7. Compute $$G_2(k) = \frac{1}{q}\{H_2(k) - H_2(M)v_k^2 - \gamma_{M+1}^2 F(M-k)\}.$$

The two matrix-vector products that generate $G_1(k)$ and $G_2(k)$ from the samples of the current density organized in the vector j can be compactly written as a sequence of linear operations. To ease the notation, four additional linear operators are introduced, i.e. for an arbitrary vector $p=(p_0, \ldots, p_M)^T$ we define $$C_M \ p = DCT_I[p_m], \qquad (81)$$

$$N_M \ p = \frac{1}{M}\left(p_0, \ldots, p_{M-1}, \frac{1}{2}p_M\right), \qquad (82)$$

$$S_M \ p = (0, p_0, \ldots, p_{M-2}, 2p_{M-1})^T, \qquad (83)$$

$$P_M \ p = p_M, \qquad (84)$$

$$P_0 \ p = p_0, \qquad (85)$$

i.e. $C_M$ now represents the DCT of type I, $N_M$ is a diagonal normalization matrix, $S_M$ is a shifting matrix combined with a multiplication, and $P_M$ is a projection operator that sifts out the last entry of the vector. The matrix representation of $S_M$ is given by $$S_M = \begin{pmatrix} 0 & \cdots & \cdots & \cdots & \cdots & 0 \\ 1 & 0 & & & & 0 \\ 0 & 1 & 0 & & & \vdots \\ \vdots & 0 & 1 & 0 & & \vdots \\ \vdots & & \ddots & \ddots & \ddots & \vdots \\ \vdots & & & 0 & 1 & 0 & \vdots \\ \vdots & \cdots & \cdots & \cdots & 0 & 2 & 0 \end{pmatrix}, \qquad (86)$$

and those of $P_0$ and $P_M$ are $$P_0 = (1,0,\ldots,0) \ P_M = (0,\ldots,0,1) \qquad (87)$$

With these definitions, we can express the matrix-vector products for $G_1=(G_1(0), \ldots, G_1(M))^T$ and $G_2=(G_2(0), \ldots, G_2(M))^T$ as $$G_1 = \frac{1}{q}\{[(I_M - v^1 P_0)C_M S_M - F^1 P_M]A^{-1}(-q)D_M N_M C_M\}j, \qquad (88)$$

$$G_2 = \frac{1}{q}\{[(I_M - v^2 P_M)C_M S_M - F^2 P_M]A^{-1}(q)D_M N_M C_M\}j, \qquad (89)$$

where we have introduced the identity operator $I_M$ and the vectors $F^1=(F(0), \ldots, F(M))^T$ and $F^2=(F(M), \ldots, F(0))^T$.

Adjoint Matrix-Vector Product

With the help of the linear operators introduced in the preceding section, the adjoint of the two matrix-vector products can be readily constructed. In formal sense, the order of the linear operations need to be reversed and each operator has to be replaced by its adjoint. Starting from the representation for $G_1$ in Eq. (88) and denoting the adjoint by the superscript $^H$, we arrive at $$\left(\frac{1}{q}\{[(I_M - v^1 P_0)C_M S_M - F^1 P_M]A^{-1}(-q)D_M N_M C_M\}\right)^H = \qquad (90)$$

$$\frac{1}{q^*}\{C_M^H N_M^H D_M^H A^{-H}(-q)[S_M^H C_M^H(I_M^H - P_0^H \ v^{1,H}) - P_M^H \ F^{1,H}]\} =$$

$$\frac{1}{q^*}\{C_M^T N_M D_M^T A^{-H}(-q)[S_M^T C_M^T(I_M - P_0^T \ v^{1,H}) - P_M^T \ F^{1,H}]\},$$

where the latter equality is a consequence of the self-adjointness of $I_M$ and $N_M$, and the observation that the matrices $C_M$, $D_M$, $S_M$, $P_0$, $P_M$ are real-valued and therefore their adjoint is equal to their transpose. All of the adjoints or transposes of the individual matrices are readily established and programmed. The only more involved adjoint is that of $A^{-H}(-q)$, but this can be performed via the LAPACK routine zgttrs that employs the LU factorization (obtained via zgttrf) of $A(-q)$ and therefore the corresponding matrix-vector product is available via this routine.

Finally, the adjoint of the representation for $G_2$ in Eq. (89) yields $$\left(\frac{1}{q}\{[(I_M - v^2 P_M)C_M S_M - F^2 P_M]A^{-1}(q)D_M N_M C_M\}\right)^H = \qquad (91)$$

$$\frac{1}{q^*}\{C_M^T N_M D_M^T A^{-H}(q)[S_M^T C_M^T(I_M - P_M^T \ v^{2,H}) - P_M^T \ F^{2,H}]\}.$$

Note that the matrix $A^{-H}(q)=-A^{-H}(-q)$ and therefore the LU decomposition of $A(-q)$ in combination with the LAPACK routine zgttrs can be used to perform this part of the adjoint matrix-vector product.

Connecting Multiple Slices

The Chebyshev expansion works best when all the components of the contrast-current density $j_m(z)$ in Eq. (1) are continuously differentiable to very high order. In that case, interpolation estimates show that the error in the approximation of the Chebyshev expansion decreases exponentially with linearly increasing order of the polynomials. However, the differentiability of the contrast-current density depends on the geometry of the grating and its material composition. When the material composition changes abruptly at a certain value of the longitudinal, aperiodic coordinate z or when the geometry of the grating exhibits a kink or discontinuity, the contrast-current density is potentially discontinuous or has components with a discontinuous first derivative.

The poor convergence of the Chebyshev expansion in case of discontinuities or discontinuous derivative can be mitigated by splitting up the interval of the expansion for the contrast-current density into smaller subintervals, or slices, such that the contrast-current density is continuously differentiable to high order on the interior of each slice. Suppose we expect a discontinuity at $z=a_1$, then the interval [a,b] is partitioned into the slices $[a,a_1]$ and $[a_1,b]$. A separate Chebyshev expansion for the contrast-current density is then defined on each slice and the previously described method of integrating the contrast-current density together with the Green's function, as given in Eq. (1), can be carried out per slice. Alternatively, one can choose to employ a Chebyshev expansion on one subinterval and another type of expansion, e.g. a piecewise expansion, on another subinterval. Also in such a case, one can employ the integration methods per slice that have already been documented and the only question that remains to be answered is how to couple the contribution from one slice to the other.

To answer this question, we concentrate on the integral $G_1(z)$ in Eq. (1), since the approach is analogous for $G_2(z)$. For the case of two slices, i.e. the intervals $[a,a_1]$ and $[a_1,b]$, we have the following two cases to consider: the observation coordinate z lies in the interval $[a,a_1]$ or in the interval $(a_1,b]$. The former case yields no coupling between the two slices, since the interval of integration starts from z=a and therefore this case can be handled by the original method of integration for one slice. For the case $z \in (a_1,b]$, we rewrite the integral $G_1(z)$ as $$G_1(z) = \int_a^z j_{i,m}(z')\exp[-\gamma_m(z-z')]dz' \qquad (92)$$

$$= \int_a^{a_1} j_{i,m}(z')\exp[-\gamma_m(z-z')]dz' +$$

$$\int_{a_1}^z j_{i,m}(z')\exp[-\gamma_m(z-z')]dz'$$

$$= \exp[-\gamma_m(z-a_1)]\int_a^{a_1} j_{i,m}(z')\exp[-\gamma_m(a_1-z')]dz' +$$

$$\int_{a_1}^z j_{i,m}(z')\exp[-\gamma_m(z-z')]dz'$$

$$= \exp[-\gamma_m(z-a_1)]G_1(a_1) + \int_{a_1}^z j_{i,m}(z')\exp[-\gamma_m(z-z')]dz',$$

The final expression above shows that coupling between the two slices takes the form of an exponential function times the already computed constant $G_1(a_1)$, which has been obtained already from the integration over the slice $[a,a_1]$. The second integral is a standard integration over a single slice, which has already been discussed previously. Hence the coupling between two or more slices is simply adding an extra term that evolves as an exponential function of the observation point z times an already computed contribution from the end point of the previous slice. When a Chebyshev expansion is used on the slice $[a_1,b]$, then the required exponential function in the above result has already been computed in the form of the vector $v^1(k)$ defined in Section 7 and the additional contribution from the slice $[a,a_1]$ can be readily merged with the constant $H_1(0)$ in step 6 of the execution phase of the full matrix-vector product, to reach maximum efficiency in the number of floating-point operations.

In the embodiment described above, a Chebyshev expansion has been used as an alternative to the piecewise-linear expansion along the longitudinal, aperiodic (z) direction for the expansion of the contrast current density that has been used in a volume integral method of calculating electromagnetic scattering properties. For numerical stability, a regularization step was used to compute the Green's function interaction with the Chebyshev expansion of the contrast current density. The resulting algorithm is numerically stable and efficient, i.e. O(N log N) where N is the number of sample points along z. Numerical tests show that the Chebyshev expansion in a volume integral method exhibits exponential convergence of the reflection coefficients. As a consequence, the Chebyshev expansion is competitive and often faster in terms of computation time when compared with the a piecewise-linear expansion in a volume integral method, especially when the number of samples per slice is large in case of the piecewise-linear expansion. This happens when a slice is thick with respect to the (local) wavelength. Another case when many piecewise-linear samples are needed, is when the number of Fourier modes in the transverse direction is high. A secondary effect is that the memory requirement of the volume integral method will decrease when fewer samples are needed.

It is also possible to implement the Chebyshev expansion along side an existing piecewise-linear expansion, and/or alongside a Chebyshev expansion with different coefficients, and/or alongside a Legendre expansion, in such a way that a choice for a particular expansion can be made for each slice separately. This allows for different expansions to be used. For example, the piecewise-linear expansion is most expedient for thin slices with very few samples whereas the Chebyshev expansion is more efficient when a slice is thick. The choice for the number of samples per slice in case of a Chebyshev expansion should reflect that a DCT is most efficient when the length of its corresponding FFT is factorizable into small primes, i.e. typically 2, 3, and 5.

Figure 17A:
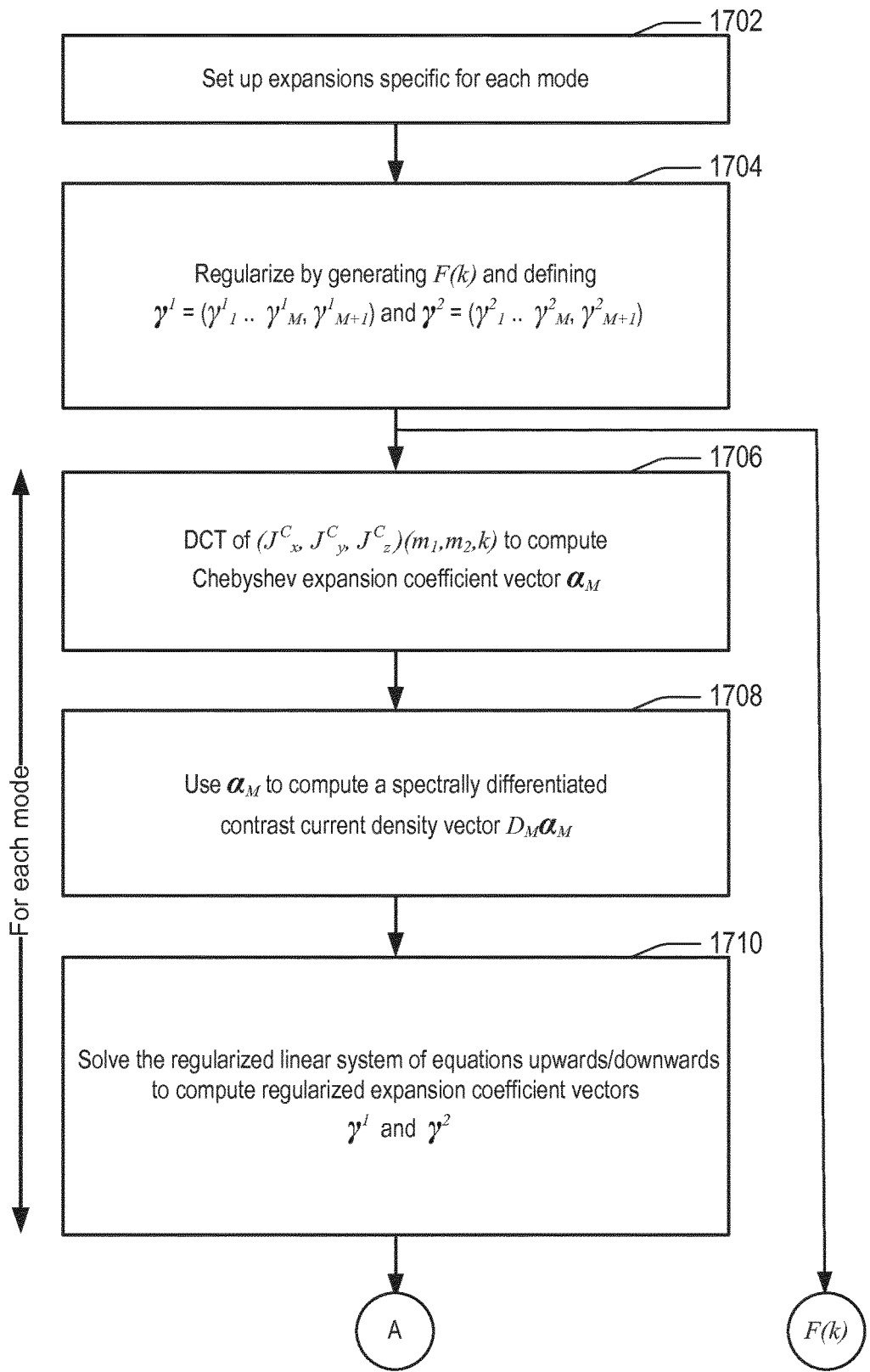
FIGS. 17A and 17B are a flow chart of a method in accordance with an embodiment of the present invention.
Figure 17B:
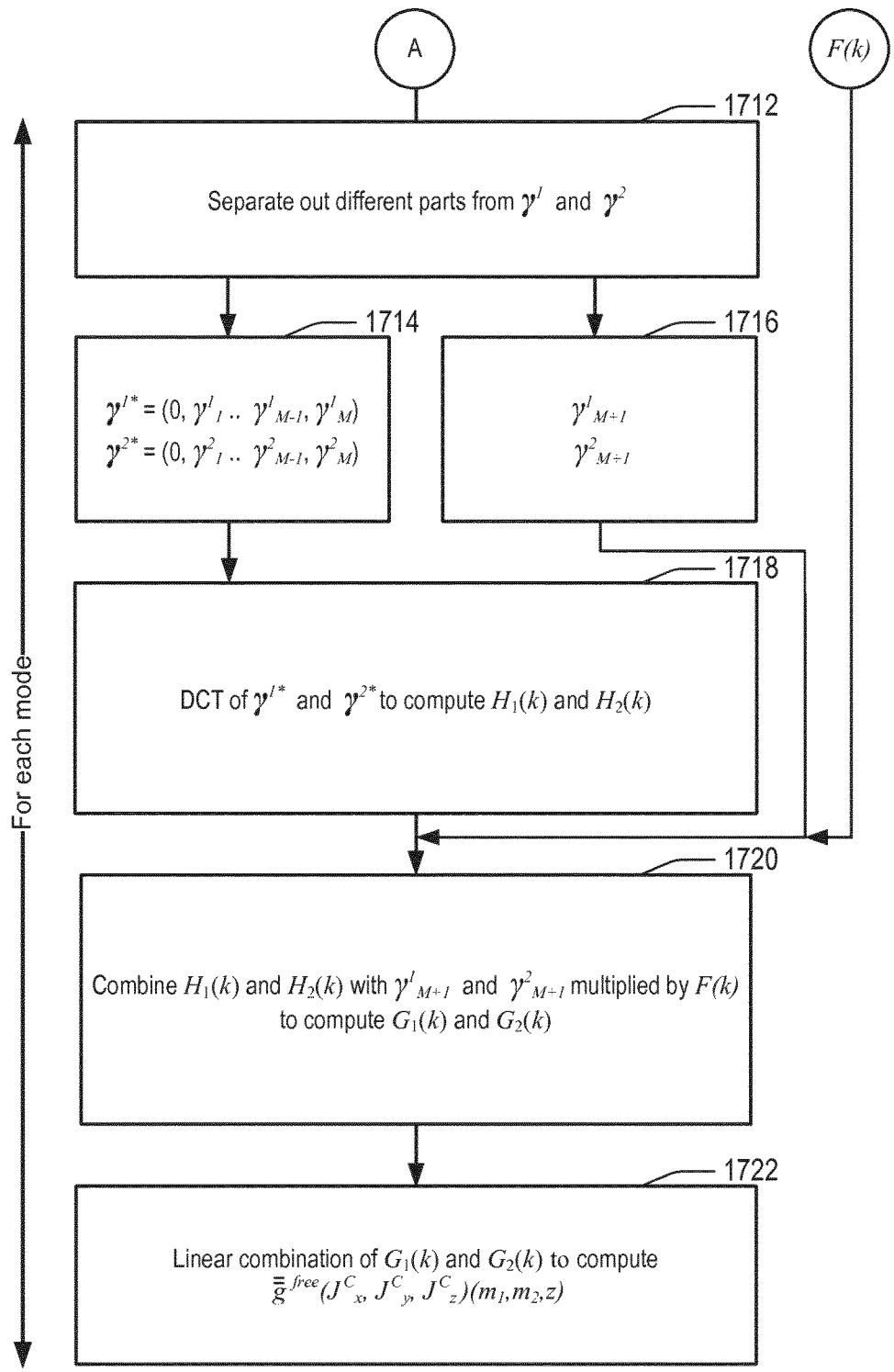

FIGS. 17A and 17B are a flow chart of a method in accordance with an embodiment of the present invention. The steps of FIGS. 17A and 17B may be substituted for the steps identified with dashed boxes as 1150 (steps 1116 to 1120), 1350 (steps 1116 to 1120) and 1550 (steps 1506 to 1510) in FIGS. 11, 13 and 15 respectively. These steps are more generally identified with dashed boxes as 1250 and 1450 in FIGS. 12 and 14 respectively. The embodiment is a method of calculating electromagnetic scattering properties of a structure, the structure including materials of differing properties and the structure being periodic in at least one lateral direction and extending in a direction orthogonal with respect to the at least one lateral direction, in this example a z direction. The method involves numerically solving a volume integral equation for electromagnetic scattering for a plurality of modes in the at least one lateral direction, by performing, for each respective mode, integration of a pseudo-spectral (in this example Chebyshev) polynomial expansion in the orthogonal direction multiplied by a 1D Green's function using the same sample points in the orthogonal direction for all of the plurality of modes, wherein the integration is performed by solving a regularized linear system of equations. The steps in FIGS. 17A and 17B are:

In step 1702, set up expansions specific for each mode.

In step 1704, regularize by: generating a function F(k) at sample points in z (Chebyshev nodes) comprising coefficients prone to conditioning-related errors and by modifying the linear system to compensate for F(k) by defining regularized upwards/downwards expansion coefficient vectors $\gamma^1 = (\gamma^1_1 \ldots \gamma^1_M, \gamma^1_{M+1})$ and $\gamma^2 = (\gamma^2_1 \ldots \gamma^2_M, \gamma^2_{M+1})$. Thus the linear system of equations is regularized by modifying the linear system to compensate for expansion coefficients prone to conditioning-related errors by defining an extended regularized expansion coefficient vector $(\gamma^1, \gamma^2)$. The term "extended" in this example includes adding a row to a vector and removing the first entry of the vector. The skilled person will appreciate that the extending is done in the context of a regularization scheme and it is the introduction of information, or the capacity to hold information in the solution, that is meant by the extending. Optionally, the step of regularizing the linear system of equations may include generating a function (F(k)) at sample points in the orthogonal direction, the function comprising expansion coefficients prone to conditioning-related errors, such that the modifying of the linear system compensates for the function (F(k)).

Optionally, the generating of the function (F(k)) at sample points in the orthogonal direction uses a recurrence formula.

In step 1706, use a discrete transformation (DCT when using a Chebyshev expansion) of sampled values of current density $(J_x^c, J_y^c, J_z^c)(m_1, m_2, z)$ at sample points in z (Chebyshev nodes) to compute a (Chebyshev) expansion coefficient vector $\alpha_M$.

In step 1708, use the (Chebyshev) expansion coefficient vector $\alpha_M$ to compute a spectrally differentiated contrast current density vector $D_M \alpha_M$.

In step 1710, perform integration of the (Chebyshev) expansion for the contrast current density times upwards/downward constituents of a 1D Green's function (corresponding to A(-q) and A(q)) by solving the regularized linear system of equations upwards/downwards across the z domain to compute regularized expansion coefficient vectors $\gamma^1$ and $\gamma^2$. Thus the regularized linear system of equations is solved between first and second discrete transformation steps to compute values of the regularized expansion coefficient vector $(\gamma^1, \gamma^2)$.

In step 1712, separate out different parts from the computed regularized expansion coefficient vectors $\gamma^1$ and $\gamma^2$.

1714 and 1716 show the different parts. In 1714, the non-extended upwards and downwards parts $\gamma^{1*} = (0, \gamma^1_1 \ldots \gamma^1_{M-1}, \gamma^1_M)$ and $\gamma^{2*} = (0, \gamma^2_1, \ldots, \gamma^2_{M-1}, \gamma^2_M)$ are shown. In practice separation of these parts may be done by copying the arrays storing the vectors $\gamma^1$ and $\gamma^2$, and modifying the arrays. In this example, the last entry of each array is removed and copied into storage for step 1716 and the first entry is set to zero. Although zero was chosen here, other values may be used. The extra entry was inserted in order to have the vector the correct length for matrix multiplication.

In 1716, the upwards and downwards computed entries $\gamma^1_{M+1}$ and $\gamma^2_{M+1}$ are shown. In an embodiment in which F(k) is not used, these entries may be discarded (and not even separated out).

In step 1718, use a second discrete transformation (DCT when using a Chebyshev expansion) of the non-extended upwards and downwards parts $\gamma^{1*}$ and $\gamma^{2*}$ of the regularized expansion coefficient vectors $\gamma^1$ and $\gamma^2$ to compute regularized integrals $H_1(k)$ and $H_2(k)$ at sample points in z. Thus the second discrete transformation step is applied to a non-extended part $(\gamma^{1*}, \gamma^{2*})$ of the regularized expansion coefficients vector $(\gamma^1, \gamma^2)$ to compute a regularized integral $H_1(k)$, $H_2(k)$ at sample points in the orthogonal direction. In an embodiment in which F(k) is not used, and the entries $\gamma^1_{M+1}$ and $\gamma^2_{M+1}$ are discarded, at this stage it is possible to perform a linear combination of the regularized integrals $H_1(k)$ and $H_2(k)$ to compute the scattered electromagnetic field $\bar{g}^{free}(J_x^c, J_y^c, J_z^c)(m_1, m_2, z)$ in the z domain in the absence of reflections. This result is equivalent to the result of the steps identified as 1150, 1350 and 1550 in FIGS. 11, 13 and 15 respectively. Thus by inserting the above steps of FIGS. 17A and 17B into volume integral methods as described with reference to FIGS. 11 to 15, electromagnetic scattering properties of the structure may be calculated using results of the numerical solution, in this example, using the computed regularized integral ($H_1(k)$ and $H_2(k)$).

In an embodiment in which F(k) is used, and the entries $\gamma^1_{M+1}$ and $\gamma^2_{M+1}$ are not discarded, instead of the linear combination of the regularized integrals $H_1(k)$ and $H_2(k)$, steps 1720 and 1722 may be used to further improve performance. In step 1720, the regularized integrals $H_1(k)$ and $H_2(k)$ are combined with the entries $\gamma^1_{M+1}$ and $\gamma^2_{M+1}$ multiplied by the function F(k) comprising coefficients prone to conditioning-related errors to compute the final integrals $G_1(k)$ and $G_2(k)$ at sample points in z. Thus the method may further comprises the step 1720, after the discrete transformation step, of combining the regularized integral ($H_1(k)$ and $H_2(k)$) with an extension part ($\gamma^1_{M+1}$, $\gamma^2_{M+1}$) of the regularized expansion coefficients vector ($\gamma^1$, $\gamma^2$) multiplied by the function (F(k)) to compute a further integral ($G_1(k)$ and $G_2(k)$) at sample points in the orthogonal direction.

In step 1722, perform a linear combination of the final integrals $G_1(k)$ and $G_2(k)$ to compute the scattered electromagnetic field $\bar{g}^{free}(J_x^c, J_y^c, J_z^c)(m_1, m_2, z)$ in the z domain in the absence of reflections. This result is equivalent to the result of the steps identified as 1150, 1350 and 1550 in FIGS. 11, 13 and 15 respectively. By inserting the above steps of FIGS. 17A and 17B, including steps 1720 and 1722, into volume integral methods as described with reference to FIGS. 11 to 15, electromagnetic scattering properties of the structure may be calculated using the computed further integral ($G_1(k)$ and $G_2(k)$).

In the embodiment described with reference to FIGS. 17A and 17B, the pseudo-spectral polynomial expansion is a Chebyshev expansion, the discrete transforms are discrete cosine transforms and the sample points in the orthogonal directions are Chebyshev nodes. Furthermore, the Chebyshev nodes include the endpoints of a domain in the orthogonal direction over which the integration is being performed. Chebyshev expansions have a relation between samples on a specific grid and a DCT, therefore can be implemented efficiently using FFTs.

In another embodiment, the pseudo-spectral polynomial expansion is a Legendre expansion and the discrete transforms are discrete Legendre transforms.

The proposed pseudo-spectral polynomial expansion with regularization yields shorter computation times and requires less memory for gratings that are high in terms of wavelengths. For gratings up to about 0.2 wavelengths high, the gain in computation time is relatively low, i.e. a factor of 2, but for gratings with a height of several wavelengths, for example a grating used in metrology for Extreme Ultra Violet (EUV) lithography, a factor of 15 to 20 improvement in computation time can be achieved. Regarding memory, the gain is directly proportional to the number of samples required, i.e. memory savings from a factor of 8 to a factor of more than 20 have been observed.

Furthermore, embodiments described herein can be combined with the already existing low-order expansions (for example piecewise-linear) in the sense that particular parts of a grating (for example a thin layer) can be expanded with a low-order expansion and other parts, which are long in terms of the wavelength, are expanded in a pseudo-spectral polynomial expansion. This yields an overall algorithm that exploits the strong points of each expansion.

Figure 18:
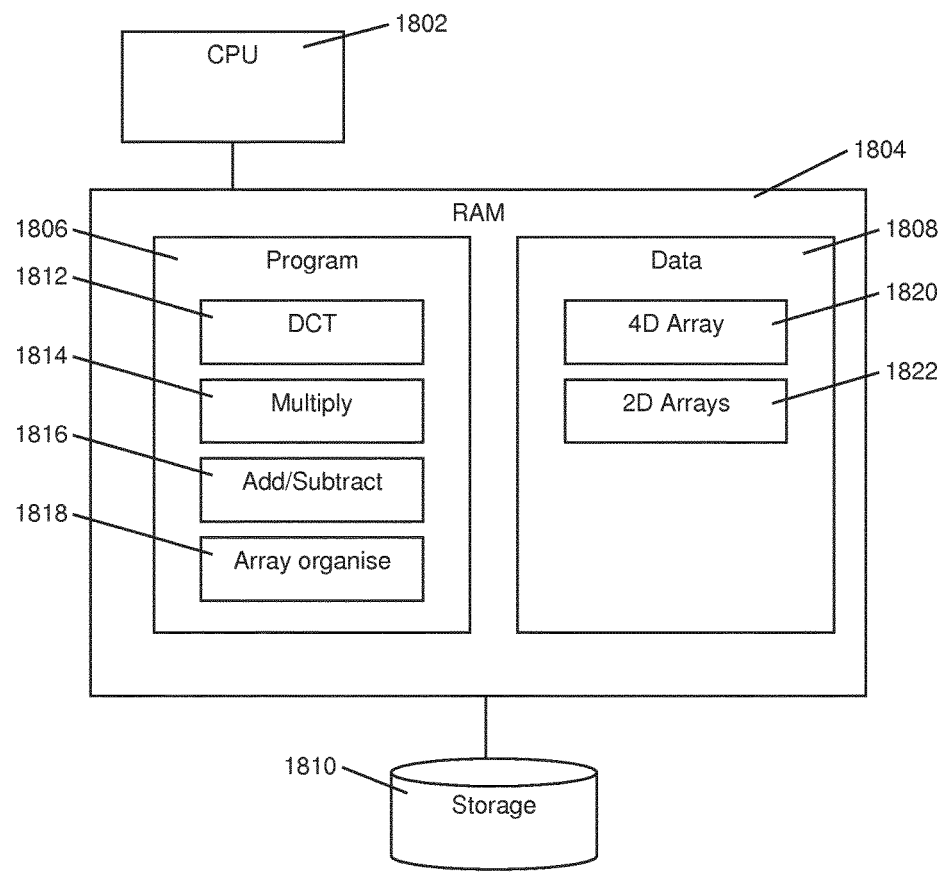
FIG. 18 depicts in schematic form a computer system configured with programs and data in order to execute a method in accordance with an embodiment of the present invention.

FIG. 18 shows in schematic form a computer system configured with programs and data in order to execute a method in accordance with an embodiment to the present invention. The computer system comprises a central processing unit (CPU) 1802 and random access memory (RAM) 1804 which is used to store the program instructions 1806 and data 1808 during execution of the program. The computer system also includes disk storage 1810 that is used to store program instructions and data before and after the execution of the program.

The program instructions 1806 include Discrete Cosine Transform (DCT) routines 1812, matrix multiplication functions 1814, other arithmetic functions such as addition and subtraction 1816 and array organizing functions 1818. The data 1808 comprises the 4D array 1820 and 2D arrays 1822 used during calculation of the solution of the VIM system. Other conventional computer components for input and output are not shown.

In embodiments of the present invention a Fourier series expansion can be used to analyze aperiodic structures by employing perfectly matched layers (PMLs), or other types of absorbing boundary conditions to mimic radiation towards infinity, near the boundary of the unit cell on which the Fourier expansions are used.

Embodiments of the present invention may be implemented in accordance with the reconstruction methods described with reference to FIGS. 5 and 6 to provide a method of reconstructing an approximate structure of an object from a detected electromagnetic scattering property arising from illumination of the object by radiation.

Embodiments of the present invention may be implemented by implementing the methods described herein on the processing units PU described with reference to FIGS. 3 and 4 to provide an inspection apparatus for reconstructing an approximate structure of an object.

The processors described with reference to FIGS. 3, 4 and 18 may operate under the control of computer programs containing one or more sequences of machine-readable instructions for calculating electromagnetic scattering properties of a structure, the instructions being adapted to cause one or more processors to perform the methods described herein.

Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The methods according to embodiments of the present invention described above may be incorporated into the forward diffraction model for reconstructing an approximate structure of an object (not limited to 1D-periodic) from a detected electromagnetic scattering property, such as a diffraction pattern, arising from illumination of the object by radiation, as described above with reference to FIGS. 5 and 6. The processing unit PU described above with reference to FIGS. 3 and 4 may be configured to reconstruct an approximate structure of an object using this method.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The term "electromagnetic" encompasses electric and magnetic.

The term "electromagnetic scattering properties" encompasses reflection and transmission coefficients and scatterometry measurement parameters including spectra (such as intensity as a function of wavelength), diffraction patterns (intensity as a function of position/angle) and the relative intensity of transverse magnetic- and transverse electric-polarized light and/or the phase difference between the transverse magnetic- and transverse electric-polarized light. Diffraction patterns themselves may be calculated for example using reflection coefficients.

Thus, although embodiments of the present invention are described in relation to reflective scattering, the invention is also applicable to transmissive scattering.

The term "regularization" refers to a process of introducing additional information in order to solve an ill-posed problem or to prevent overfitting.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

REFERENCES

[1] L. M. Delves and J. L. Mohamed. *Computational methods for integral equations*. Cambridge University Press, 1985.
[2] S.-Y. Kang, I. Koltracht, and G. Rawitscher. Nyström-Clenshaw-Curtis quadrature for integral equations with discontinuous kernels. *Mathematics of computation*, 72:729-756, March 2002.
[3] W. H. Press, S. A. Teukolsky, W. T. Vetterling, and B. P. Flannery. *Numerical Recipes in Fortran 77: the art of scientific computing*. Cambridge University Press, 2nd edition, 1992.
[4] A. Quarteroni and A. Valli. *Numerical Approximation of Partial Differential Equations*. Springer Series in Computational Mathematics. Springer, 1994.
[5] T. Hasegawa and T. Torii. Indefinite integration of oscillatory functions by the chebyshev series expansion. *Journal of Computational and Applied Mathematics*, 17:21-29, 1987.

What is claimed is:

1. A method of calculating electromagnetic scattering properties of a structure, the structure including materials of differing properties and the structure being periodic in at least one lateral direction and extending in a direction orthogonal with respect to the at least one lateral direction, the method comprising:
numerically solving a volume integral equation for electromagnetic scattering for a plurality of modes in the at least one lateral direction, by performing, for each respective mode, integration of a pseudo-spectral polynomial expansion in the orthogonal direction multiplied by a 1D Green's function using the same sample points in the orthogonal direction for all of the plurality of modes, wherein the integration is performed by solving a regularized linear system of equations; and
calculating electromagnetic scattering properties of the structure using results of the numerical solution.

2. The method of claim 1, further comprising:
regularizing the linear system of equations by modifying the linear system to compensate for expansion coefficients prone to conditioning-related errors by defining an extended regularized expansion coefficient vector ($\gamma 1$, $\gamma 2$);
solving the regularized linear system of equations between first and second discrete transformation steps to compute values of the regularized expansion coefficient vector ($\gamma 1$, $\gamma 2$);
applying the second discrete transformation step to a non-extended part ($\gamma 1^*$, $\gamma 2^*$) of the regularized expansion coefficients vector ($\gamma 1$, $\gamma 2$) to compute a regularized integral (H1($k$), H2($k$)) at sample points in the orthogonal direction; and
wherein the step of calculating electromagnetic scattering properties of the structure uses the computed regularized integral (H1($k$) and H2($k$)).

3. The method of claim 2, wherein the regularizing the linear system of equations comprises generating a function (F(k)) at sample points in the orthogonal direction, the function comprising expansion coefficients prone to conditioning-related errors, such that the modifying of the linear system compensates for the function (F(k)),
and the method further comprises, after the discrete transformation, of combining the regularized integral (H1($k$) and H2($k$)) with an extension part ($\gamma 1 M+1$, $\gamma 2 M+1$) of the regularized expansion coefficients vector ($\gamma 1$, $\gamma 2$) multiplied by the function (F(k)) to compute a further integral (G1($k$) and G2($k$)) at sample points in the orthogonal direction,
and wherein the calculating electromagnetic scattering properties of the structure uses the computed further integral (G1($k$) and G2($k$)).

4. The method of claim 3, wherein the generating of the function (F(k)) at sample points in the orthogonal direction uses a recurrence formula.

5. The method of claim 1, wherein the pseudo-spectral polynomial expansion is a Chebyshev expansion, the discrete transforms are discrete cosine transforms and the sample points in the orthogonal directions are Chebyshev nodes.

6. The method of claim 5, wherein the Chebyshev nodes include the endpoints of a domain in the orthogonal direction over which the integration is being performed.

7. The method of claim 1, wherein the pseudo-spectral polynomial expansion is a Legendre expansion and the discrete transforms are discrete Legendre transforms.

8. A method of reconstructing an approximate structure of an object from a detected electromagnetic scattering property arising from illumination of the object by radiation, the method comprising:
estimating at least one structural parameter;
determining at least one model electromagnetic scattering property from the at least one structural parameter;
comparing the detected electromagnetic scattering property to the at least one model electromagnetic scattering property; and
determining an approximate object structure based on the result of the comparison,
wherein the model electromagnetic scattering property is determined by:
numerically solving a volume integral equation for electromagnetic scattering for a plurality of modes in the at least one lateral direction, by performing, for each respective mode, integration of a pseudo-spectral polynomial expansion in the orthogonal direction multiplied by a 1D Green's function using the same sample points in the orthogonal direction for all of the plurality of modes, wherein the integration is performed by solving a regularized linear system of equations; and
calculating electromagnetic scattering properties of the structure using results of the numerical solution.

9. The method according to claim 8, further comprising:
arranging a plurality of the model electromagnetic scattering properties in a library: and
the comparing comprises matching the detected electromagnetic scattering property to contents of the library.

10. The method according to claim 8, further comprising iterating the steps of determining at least one model electromagnetic scattering property, and comparing the detected electromagnetic scattering property wherein the structural parameter is revised based on the result of the step of comparing in a previous iteration.

11. An inspection apparatus for reconstructing an approximate structure of an object, the inspection apparatus comprising:
- an illumination system configured to illuminate the object with radiation;
- a detection system configured to detect an electromagnetic scattering property arising from the illumination; and
- a processor configured to:
  - estimate at least one structural parameter;
  - determine at least one model electromagnetic scattering property from the at least one structural parameter;
  - compare the detected electromagnetic scattering property to the at least one model electromagnetic scattering property; and
  - determine an approximate object structure from a difference between the detected electromagnetic scattering property and the at least one model electromagnetic scattering property,
- wherein the processor is configured to determine the model electromagnetic scattering property using a method comprising:
  - numerically solving a volume integral equation for electromagnetic scattering for a plurality of modes in the at least one lateral direction, by performing, for each respective mode, integration of a pseudo-spectral polynomial expansion in the orthogonal direction multiplied by a 1D Green's function using the same sample points in the orthogonal direction for all of the plurality of modes, wherein the integration is performed by solving a regularized linear system of equations; and
  - calculating electromagnetic scattering properties of the structure using results of the numerical solution.

12. A computer program product containing one or more sequences of machine-readable instructions for calculating electromagnetic scattering properties of a structure, the instructions being adapted to cause one or more processors to perform a method comprising:
- numerically solving a volume integral equation for electromagnetic scattering for a plurality of modes in the at least one lateral direction, by performing, for each respective mode, integration of a pseudo-spectral polynomial expansion in the orthogonal direction multiplied by a 1D Green's function using the same sample points in the orthogonal direction for all of the plurality of modes, wherein the integration is performed by solving a regularized linear system of equations; and
- calculating electromagnetic scattering properties of the structure using results of the numerical solution.

* * * * *

UNITED STATES PATENT AND TRADEMARK OFFICE
CERTIFICATE OF CORRECTION

PATENT NO. : 9,766,552 B2
APPLICATION NO. : 14/915804
DATED : September 19, 2017
INVENTOR(S) : Martijn Constant Van Beurden Page 1 of 1

It is certified that error appears in the above-identified patent and that said Letters Patent is hereby corrected as shown below:

On the Title Page

(57) Abstract, Line 10, after "multiplied by a" please delete "ID" and insert --1D--.

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*